United States Patent [19]

Van Wagenen et al.

[11] Patent Number: 4,784,486

[45] Date of Patent: Nov. 15, 1988

[54] MULTI-CHANNEL MOLECULAR GAS ANALYSIS BY LASER-ACTIVATED RAMAN LIGHT SCATTERING

[75] Inventors: Richard A. Van Wagenen; Jeffrey D. Geisler; Donald E. Gregonis; Dennis L. Coleman, all of Salt Lake City, Utah

[73] Assignee: Albion Instruments, Salt Lake City, Utah

[21] Appl. No.: 106,791

[22] Filed: Oct. 6, 1987

[51] Int. Cl.$^4$ .................. G01J 3/44; G01N 21/65
[52] U.S. Cl. .................................................. 356/301
[58] Field of Search .................. 356/301, 339, 343

[56] References Cited

U.S. PATENT DOCUMENTS

| | | | |
|---|---|---|---|
| 3,704,951 | 12/1972 | Chupp | 356/301 |
| 3,723,007 | 3/1973 | Leonard | 356/301 |
| 4,410,271 | 10/1983 | Matthews | 356/301 |
| 4,630,923 | 12/1986 | Tans et al. | 356/301 |
| 4,648,714 | 3/1987 | Benner et al. | 356/301 |
| 4,676,639 | 6/1987 | Van Wagenen | 356/301 X |

FOREIGN PATENT DOCUMENTS

| | | |
|---|---|---|
| 2937352 | 6/1981 | Fed. Rep. of Germany . |
| 2723939 | 5/1983 | Fed. Rep. of Germany . |
| 47-28956 | 7/1972 | Japan .................. 356/301 |

OTHER PUBLICATIONS

Hickman et al., "Intracavity Laser Raman Spectroscopy Using a Commercial Laser", *Applied Spectroscopy*, vol. 27, No. 6, 1973, pp. 425–427.
Hercher et al., "An Efficient Intracavity Laser Raman Spectrometer", *Applied Spectroscopy*, vol. 32, No. 3, 1978, pp. 298–302.
Neely et al., "Modification of a Commercial Argon Ion Laser . . . Scattering", *Applied Spectroscopy*, vol. 26, No. 5, 1972, pp. 553–555.
Demtroder, Laser Spectroscopy, Basic Concepts and Instrumentation, Springer–Verlag Berlin Heidelberg, New York, 1981, pp. 652–654.
Weber et al., "High–Resolution Raman Spectroscopy of Gases . . . Excitation", *J. of Optical Society of America*, vol. 57, No. 1, Jan. 1967, pp. 19–28.
Weber et al., "High–Resolution Raman Spectroscopy . . . Single–Mode Argon Laser", *J. of Optical Society of America*, vol. 62, No. 3, Mar. 1972, pp. 428–432.

(List continued on next page.)

*Primary Examiner*—F. L. Evans
*Attorney, Agent, or Firm*—Knobbe, Martens, Olson & Bear

[57] ABSTRACT

The concentration of multiple polyatomic gases are determined simultaneously by Raman light scattering. The gas sample is placed in a sampling cell and a polarized laser beam is passed through the cell, along a longitudinal axis. A portion of the light scattered by the gas sample is captured and detected by means of multiple collection optics-filter-detector channels. The scattered light exits the gas cell via windows located in the sides of the gas cell and enters the collection channels which are aligned with the cell windows. The cell windows are along the longitudinal axis of the laser beam and gas cell. Light scattered by the gas sample provides signals of both inelastic Raman scattered light and elastic laser scattered light which are directed to the collection channels. The optics of each channel transports the scattered light signals onto a laser line rejection filter where the elastic scattered laser signals are attenuated. The remaining inelastic Raman scattered signals are caused to be incident upon an interference filter which is specific to the transmission of one or more specific Raman lines. The interference filter in each collection channel is selected to a specific wavelength which is characteristic of Raman scattering from a particular polyatomic gas. The optical signals representative of these specific Raman lines passing through the interference filters are sensed by optical detectors, and amplified and converted into digital electrical pulses which are processed into simultaneous visual readouts indicative of the identity and concentration of each of the polyatomic gas molecules present in the sample of gas being analyzed.

57 Claims, 12 Drawing Sheets

OTHER PUBLICATIONS

Barrett et al., "Laser-Excited Rotation-Vibration Raman . . . Gas Samples", J. of Optical Society of America, vol. 58, No. 3, Mar. 1968, pp. 311–319.

Van Wagenen et al., "Dedicated Monitoring of Anesthetic and Respiratory Gases by Raman Scattering", *J. of Clinical Monitoring*, vol. 2, No. 4, Oct. 1986.

D. A. Long, *Raman Spectroscopy*, McGraw-Hill, Ch. 6, "Experimental Procedures", pp. 132–145 and Central Reference Section, 1977.

*Raman Spectroscopy of Gases and Liquids*, Springer-Verlag, 1979, Ch. 3, "High-Resolution . . . of Gases", pp. 71–85; Ch. 4, "Raman Scattering . . . and Liquids, 123–142.

*The Raman Effect*, vol. 2, Ch. 9, A. Weber, "High Resolution Raman Studies of Gases, pp. 581–622.

Barrett, "The Use of a Fabry–Perot Interferometer . . . Spectra of Gases", pp. 63–73 and Hill et al., Raman Scattering . . . Mutiple-Pass Cells, pp. 315–329, *Laser Raman Gas Diagnostics*, Plenum Press.

Schrotter et al., "Raman Scattering Cross Sections in Gases and Liquids", pp. 123–142.

Hill et al., "Raman Scattering with High Gain Multiple-Pass Cells", Technological Applications, pp. 315–329.

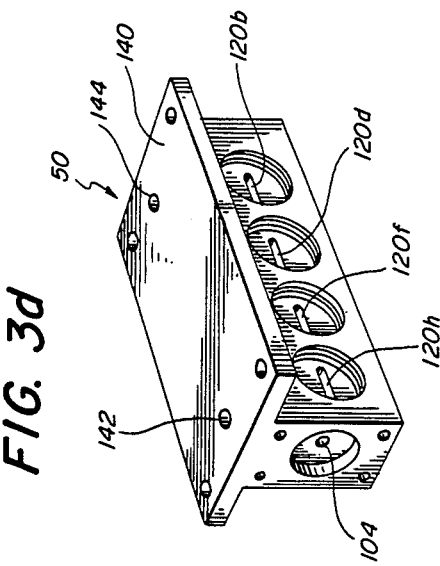
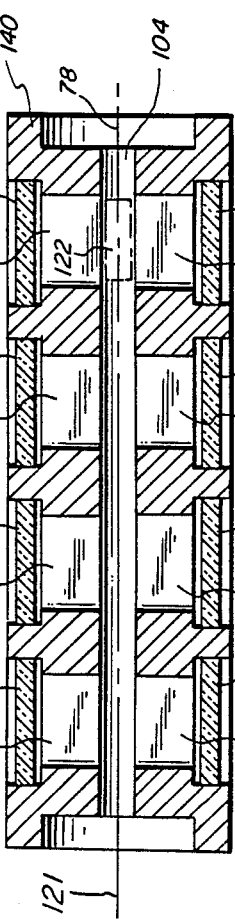
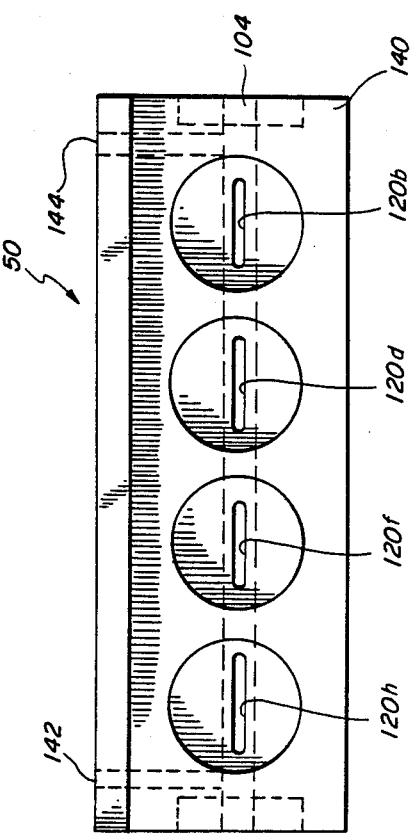

FIG. 11
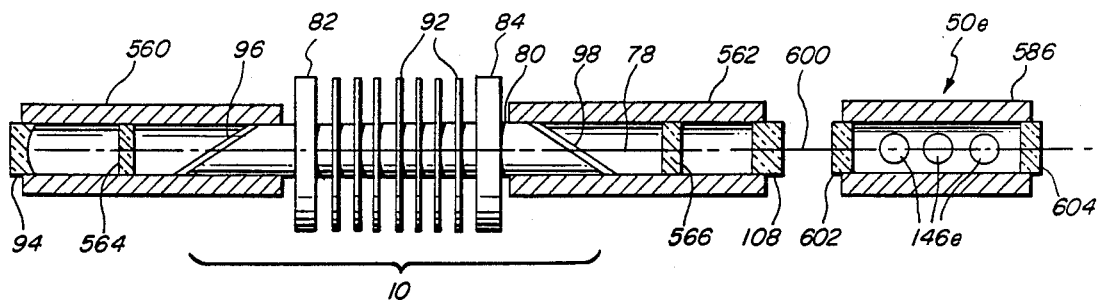
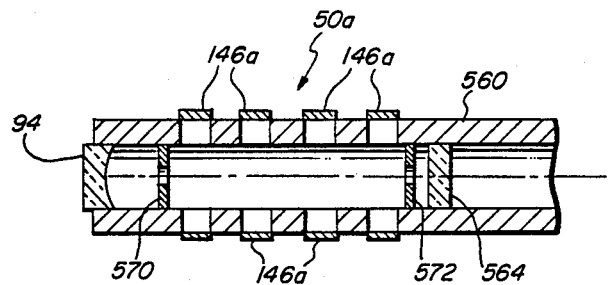
FIG. 11a
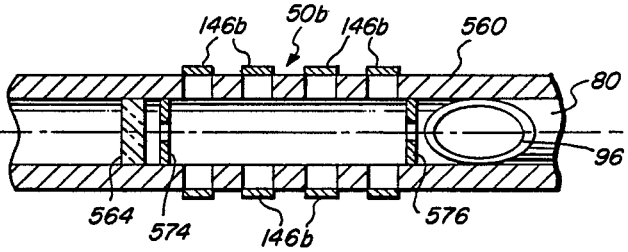
FIG. 11b
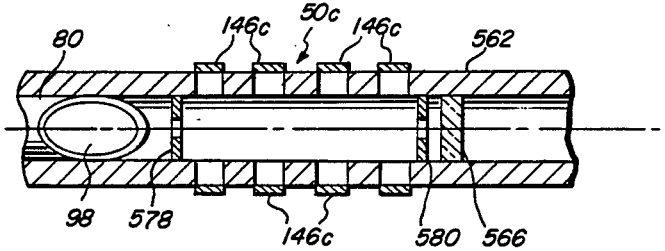
FIG. 11c
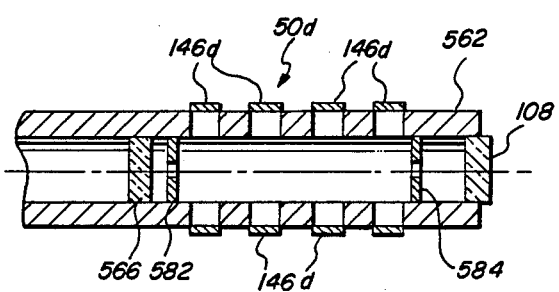
FIG. 11d

MULTI-CHANNEL MOLECULAR GAS ANALYSIS BY LASER-ACTIVATED RAMAN LIGHT SCATTERING

FIELD OF THE INVENTION

The invention relates generally to gas analysis and, more specifically, to systems for the simultaneous analysis of multiple gases by laser-induced Raman light scattering.

BACKGROUND OF THE INVENTION

Continuous breath-by-breath analysis of a patient's respiratory gases in the operating room is becoming increasingly important in improving patient safety during anesthesia. Respiratory and anesthetic gas monitoring, as well as the determination of specific cardiac and pulmonary functions which are based upon the uptake and production of specific tracer and respiratory gases, has reached a high standard of technological advancement with the development of sophisticated sensors, transducers and computers. These monitoring techniques enable quick diagnosis and treatment of unfavorable trends in the condition of a patient and lead to an improved survival rate, early extubation following surgery and a shorter time in the intensive care unit. Applications of respiratory gas and anesthetic agent monitoring include the measurement of oxygen consumption, carbon dioxide production, anesthetic agent uptake and the possibility of detecting anesthesia machine circuit disconnections and introduction of air emboli into the blood. These measurements lead to a more scientific basis for the administration of anesthetic agent. breath-by-breath monitoring of a patient's respiratory gases and simultaneous determination of multiple specific respiratory gases and anesthetic agents in the patient's system in the intensive care unit and other critical situations, can often facilitate diagnosis and treatment, anticipate and prevent the development of oncoming problems, and otherwise provide instant data for physicians and other health care personnel to use in therapeutic situations. The same may be said of the breath-by-breath analysis of gas mixtures used for non-invasive determination of cardiac output and lung function.

Respiration monitoring of the critically ill patient is now available in operating rooms and intensive care units utilizing the techniques of mass spectrometry to identify specific volatile anesthetic agents and quantify nitrogen. Multiple-bed sampeling techniques make feasible the use of an expensive, multiplexed mass spectrometer gas analyzer because it can be shared among a number of patients. Since the mass spectrometer unit is large and not easily moved from room to room, it is generally placed in a remote location and lengthy capillary tubes are used to connect the patients to the unit. This tube transport system increases the possibility of gas sample mixing, time delay, waveform distortion and disconnections, and poses inherent limitations for use in anesthesia, critical care and medical research. Furthermore, the mass spectrometer requires a vacuum system, which increases its cost and maintenance and decreases its reliability. The vacuum system also prevents use of the mass spectrometer in many situations where Helium or other inert gases are present. Inert gases are often used in laser surgery procedures to purge the location where the laser is applied to the patient. Diffusion of the inert gas into the mass spectrometer's vacuum system renders it virtually useless for respiratory gas analysis.

Alternatively, there are a variety of gas detectors based upon several different physical principles including infrared absorption, and polarographic and solid-state semiconductor analysis which, when taken together, can measure anesthetic agents and respiratory gases. Some disadvantages of these detectors are high aggregate cost, bulkiness, slow response time and poor data integration into one comprehensive display of patient parameters.

An alternative technique proposed for use in simultaneously monitoring several gases in critical care situations is based on Raman light scattering. The Raman light scattering effect occurs when monochromatic light interacts with the vibrational/rotational modes of gas molecules to produce scattered light which is frequency shifted from that of the incident radiation by the amount corresponding to the vibrational/rotational energies of the scattering gas molecules. If the incident light photon loses energy in the collision, it is re-emitted as scattered light with lower energy and consequently lower frequency than the incident photon. This inelastic scattering is termed Stokes Raman scattering. Similarly, if the incident photon gains energy in the collision, it is re-emitted as scattered light with higher energy and consequently higher frequency than the incident photon. This type of inelastic scattering is termed anti-Stokes Raman scattering. Since these energy shifts are species-specific, an analysis of the various frequency components present in the Raman scattering spectrum provides chemical identification of the gases present in the scattering volume. The intensity of the various frequency components or Raman lines provides quantification of the gases present, providing suitable calibrations have been made. The relative sensitivity to the different gases remains absolutely fixed, eliminating frequent calibration requirements. In principal, either Stokes or anti-Stokes Raman light scattering can be utilized. However, at room temperature, the Stokes Raman effect is generally more intense.

Raman techniques have been widely used for atmospheric monitoring and for combustion applications. Sensitivities better than 1 ppm have been demonstrated. A typical application of Raman scattering analysis coupled with computer-assisted signal processing techniques is reported in Lapp, et al., "*Laser Raman Gas Diagnostics,*" Plenum Press, New York/London, 1974.

Raman scattering analytical techniques are also described in the patent literature. Benner, et al. (U.S. Pat. No. 4,648,714) contains a summary of many of these, including Chupp (U.S. Pat. No. 3,704,951), Hatzenbuhler (U.S. Pat. No. 3,807,862) and Leonard (U.S. Pat. No. 3,723,007).

A system for the simultaneous detection of multiple gases is taught in Albrecht, et al., German Pat. No. DE 27 23 939 C2 (1983). This patent discloses an extracavity multi-pass sample cell having two concave mirrors which constrain an unpolarized laser beam in a region between the two concave mirrors. The two concave mirrors are oriented so that the laser beam repeatedly reflects back and forth between the two mirrors through a focused region, or region of increased light intensity. It is from this focused region that Raman scattered light from the sample under analysis is collected and analyzed. The scattered light from the focused region is collected by a series of six detector channels mounted about the focus region to provide a 360° equatorial monitoring geometry for the Raman scattered light. Each channel has collection lenses, interference filters and photon detectors. The interference filters are selected so that each channel is sensitive to a specific gas. This is accomplished by combining a broadband filter with one gas-specific filter. The six channels thus collect signals from six separate Raman lines for the simultaneous monitoring of six different gas components. This method, wherein the detector channels are arranged in an equatorial plane and are aimed at a single point of high light intensity within the cell is, by its own admission, limited to no more than six detectors due to the fact that the effective solid angle per channel for collection of Raman light from the sample corresponds to approximately an f/1 collection lens. Utilization of such a collection lens is alleged to ensure optimum exploitation of light scattering. If it is desired to monitor more than six gas components, the registered light scatter is split into several gas-specific components which are successively routed to various detectors. This is accomplished using a collection lens which directs the scattered light onto a series of interference filters and concave mirrors at an angle of incidence such that the gas to be detected at the first filter passes through to a detector with the remaining light being reflected to a concave mirror and passed to another filter through which another specific light component is filtered out. The process continues for as many filters, detectors and mirrors as required to obtain the desired number of channels. A mirror which directly reflects light from the last filter in the serial chain passes the remaining light back through the chain so that the entering and exiting directions coincide, and the light passes all filters again precise positioning of the angles of the filters and mirrors. Moreover, there is a cumulative loss of light intensity with each reflection which, after reflection from several filters and mirrors, becomes quite significant. Since Raman scattered light is considerably weaker than the incident light, it is desirable to direct, collect, filter and focus each monitored wavelength of the scattered light to the detector with a minimum number of refractions and reflections. The equatorial sampling plane geometry also requires that the laser beam be unpolarized in order to obtain adequate and uniform Raman signals from the gas sample.

An improved system for the near-simultaneous determination of multiple polyatomic gases by collection and detection of Raman scattered light which overcomes many of the limitations of the Albrecht system is disclosed by Benner, et al. (U.S. Pat. No. 4,648,714). This patent teaches a system and method, wherein a gas sample is placed in a sampling cell located in the resonant cavity of a laser. A polarized laser beam, having sufficient intensity to produce detectable signals of Raman scattered light, is passed through the cell and gas. Both inelastic Raman scattered light and elastic laser-scattered light are collected from a single focused region of the polarized laser beam by a collection lens having its optical axis perpendicular to both the axis of the laser beam and the polarization vector of the laser beam. Another portion of the scattered light is captured and redirected to the collection lens by means of a reflection mirror having an optical axis oriented perpendicular to the axis of the laser beam and located adjacent to the focused region. The mirror is external to the gas cell. The collected scattered signals are directed onto a multilayer dielectric laser line rejection filter where the scattered elastic laser signals are filtered out and the inelastic Raman scattered signals are transmitted to a rotating filter wheel containing a series of interference filters, each filter being specific to the transmission of one Raman line. The Raman lines passing through the rotating filters are sensed sequentially by means of a single detector, and amplified and converted into digital electrical pulses which are processed and converted into visual readouts which display the identity and concentration of each of the polyatomic molecules present in the gas being analyzed.

While the system disclosed in the Benner, et al. patent is a substantial improvement over prior art techniques, there are practical limitations associated with the use of a single detector and filter wheel containing numerous interference filters. For example, near-simultaneous serial sampling with a single detector requires a microprocessor fast and powerful enough to process all of the sequential data from "n" channels. It also requires that sufficient signal intensity be present at the detector for each filter position to enable the signal to be analyzed in a very short time period. Cross talk corrections between channels, e.g., the anesthetic gases and nitrous oxide channels, also require a fast microprocessor when the data are acquired serially.

A need thus exists for a device and method for simultaneously monitoring multiple gases using Raman scattering techniques which does not sacrifice performance when more than six detector channels are used. Such a device should also be capable of rapidly monitoring more than six gas species simultaneously without requiring ultra-fast electronic processors or exotic optical systems. The monitoring device should accomplish the foregoing without sacrificing the response time of the system or the accuracy of its determinations.

SUMMARY OF THE INVENTION

The present invention is a method and apparatus for the simultaneous detection and analysis of multiple gases comprising a gas sample by means of laser-induced Raman light scattering, wherein the gas sample is placed either inside or outside the resonant cavity of a laser light source. A multiplicity of dedicated optics and detectors are utilized for collecting and quantitating the Raman scattered light signals from the sample. A dedicated optics detector is utilized for each gas species being analyzed.

More specifically, the invention relates to a method and system for the continuous breath-by-breath analysis of the multiple respiratory gases and anesthetic vapor agents comprising a patient's breath wherein an incident laser beam passes through a respiratory gas sample placed either within the resonant cavity of a laser or outside the resonant cavity. A series of light collection optics and interference filters is used to transmit Raman scattered light from the sample onto appropriate detectors for quantitating each specific Raman signal, and thus each specific gas comprising the respiratory sample.

The gas analyzer of the present invention advantageously utilizes the principles of Raman scattering to provide continuous and simultaneous analysis of the multiple gases comprising a patient's breath. In contrast to the prior systems, it is cost effective and practical to dedicate use of the invention to a single patient. Single patient use improves detection response time and virtually eliminates most of the inherent limitations of a system shared by multiple patients. These advantages are achieved without sacrificing the quality of the analysis.

Gas analyzers constructed in accordance with the present invention have the reliability and flexibility necessary for routine use in the operating room, intensive care unit, recovery room and other locations where continuous monitoring of a patient's respiratory gases is indicated. The capability to simultaneously monitor multiple gas species and perform real time analysis of the concentrations of the gases enables the medical personnel to more accurately monitor the condition of the patient. Additionally, the accidental administration of the wrong type of anesthetic agent or the wrong dosage is reduced when the present invention is used, because the type and corresponding concentration of agents present in the patient's system are determined with each breath the patient takes.

The present invention may also be used in environments where prior instruments often fail. Specifically, in laser surgery, Helium gas is used to flood the area where the laser is applied to the patient. Gas analysis systems which utilize a vacuum chamber, e.g., mass spectrometers, are often rendered completely inoperable in the presence of the Helium gas. The presence of external gases does not affect the operation of the present invention, since it does not require a vacuum system. The absence of a vacuum system also improves the reliability of the present invention and reduces its acquisition and maintenance costs.

The invention advantageously comprises multiple collection regions to increase the number of gas species which can be simultaneously monitored. These multiple regions are positioned along a longitudinal axis of a beam of radiation produced by a light source. Optical signals, representative of light scattered from the gas sample, are collected by multiple collection channels positioned to receive light from the sample at the multiple collection regions along the axis of the radiation beam. The collection regions may be located at either collimated or focused regions of the beam of radiation. When collection is from a collimated region, it is preferable that the light source produce polarized light. When collection is from a focused region, it is preferable that the light source produce unpolarized light.

The present invention performs rapid data analysis for several gas species using conventional data analysis techniques and microprocessors by processing the data from several collection channels simultaneously. One feature of the invention which contributes to this efficient handling of data is the series of filters in the multiple collection channels which reject the elastically-scattered laser light (Rayleigh scatter) while passing the particular Stokes and/or anti-Stokes Raman lines of interest for the gas species of each channel.

One embodiment of the present invention provides an improved system and method for the simultaneous monitoring of multiple gases by means of polarized laser light-initiated Raman scattering. The system uses either an intracavity or extracavity sampling cell and multiple detectors which receive Stokes and/or anti-Stokes Raman line spectra from a sample. Multiple optics-filter channels, each specific to a particular gas species, comprise collection optics and a narrowband interference filter.

The present invention improves response time for determination of gas identity and concentration by utilizing a gas sampling cell, wherein the sampling volume is small and continuous, and wherein the optics-filter channels are aligned relative to the sampling cell to directly receive Raman scattered light from the gas sample.

One embodiment of the system comprises a polarized laser source, preferably containing a gas sampling cell located within the resonant cavity of the laser for enhancing the Raman scattering signal. However, a gas cell located outside the resonant cavity may also be utilized. The Raman scattered light is simultaneously directed from the gas cell onto and through a series of aligned optics-filter-detector channels. Each channel comprises (a) an optics portion including a collection lens, or a series of antireflection-coated collection lenses; (b) a filter portion which includes a laser line rejection filter to attenuate the elastically-scattered laser light and transmit the inelastically-scattered Stokes and/or anti-Stokes Raman lines arising from collisions with the gas molecules being sampled, and a narrowband interference filter chosen to pass along one or more Raman lines corresponding to discrete molecular species; (c) an optional focusing lens to focus said Raman line; and (d) a detector to receive, amplify and process said Raman line into useful data indicative of the concentration of the discrete molecular species being detected.

Typical of the amplification and detection means is a photomultiplier tube (PMT) used in conjunction with photon-counting or photocurrent electronics, or a variety of solid-state photodetectors such as, but not limited to, avalanche photodiodes, intensified diode arrays or charge-coupled devices. Thus, each gas-specific channel, comprised of a series of collection optics, interference filters, focusing optics (if desired) and detectors, senses specific select gases. The corresponding concentrations of these select gases are determined after suitable calibrations have been made. Hence, the determination of each gas is simultaneous and nearly instantaneous. Data from each detector is preferably sent to a microprocessor from which the concentration of each gas being detected can be further processed and printed out or displayed as desired. Simultaneous readings and/or waveforms of each gas, accurate to a fraction of a volume percent, may be output at any desired time interval.

DESCRIPTION OF THE DRAWINGS

FIG. 3a is a top section view of a gas sampling cell as utilized in the multi-channel, collicated beam system shown in FIG. 2.

FIG. 3b is a side view of the gas cell shown in FIG. 3a.

FIG. 3c is an end view of the gas cell in FIGS. 3a and 3b.

FIG. 3d is a perspective view of the gas cell shown in FIGS. 3a, 3b, and 3c.

FIG. 7b is a continuation of FIG. 7a.

FIG. 11 is a side view of a laser resonator and gas cell configuration showing the gas cell being located outside of the resonator cavity and also indicating intracavity locations, wherein one or more gas cells could be located.

FIGS. 11a, 11b, 11c and 11d are top view schematic diagrams of portions of the resonator shown in FIG. 11 showing how these portions can also serve as parts of an intracavity gas cell.

DETAILED DESCRIPTION OF THE INVENTION

Figure 1A:
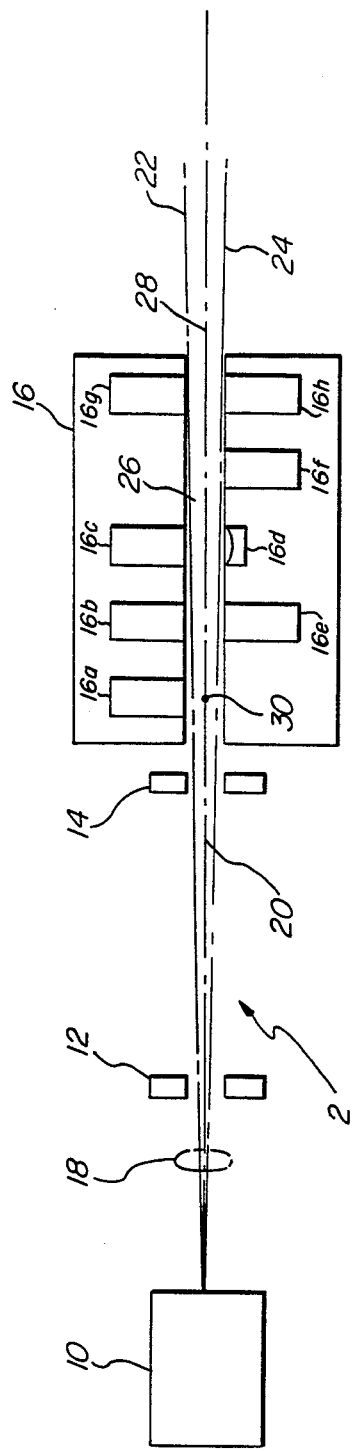
FIG. 1a is a schematic representation of one embodiment of the invention showing a multiple channel collimated beam Raman spectroscopy system.
Figure 1C:
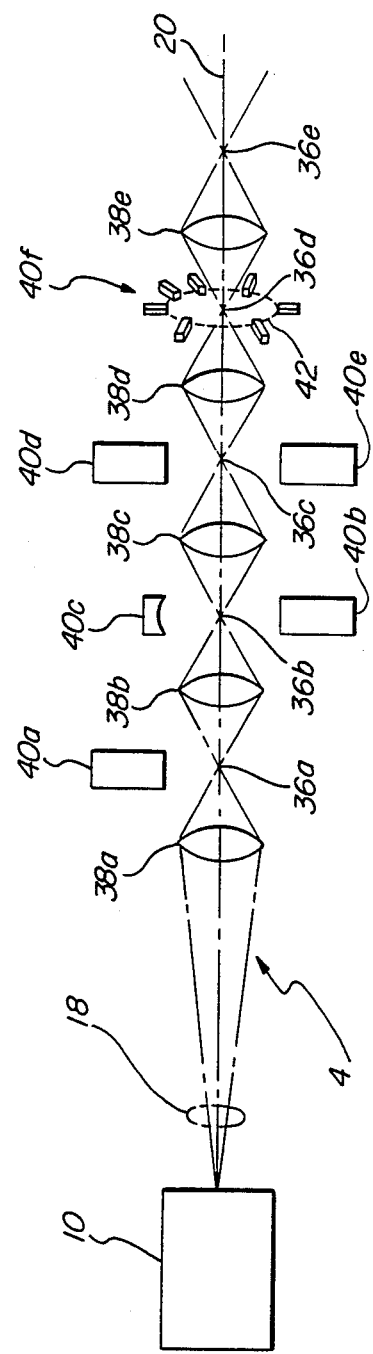
FIG. 1c is a schematic representation of one embodiment of the invention showing a multiple channel focused beam Raman spectroscopy system.

FIGS. 1a and 1c illustrate block diagram schematic representations of two Raman analysis configurations which incorporate the features of the preferred embodiment of the present invention. FIG. 1a shows a configuration 2 which will be referred to as a collimated beam system while FIG. 1c shows a configuration 4 which will be referred to as a focused beam system.

FIG. 1a shows the collimated light beam system 2 comprising a light source 10, light beam collimators 12 and 14, and multiple analysis channels 16. The analysis channels 16a through 16h are positioned adjacent a light beam 18. The light beam 18 is emitted by the light source 10 along longitudinal axis 20. A sampling region 26 having a longitudinal axis 28 substantially coincident with the longitudinal axis 20 of the light beam 18 contains a gaseous sample for analysis. The collimators 12 and 14 are positioned about the axis 20 so that as the light beam 18 passes along the axis 20, it becomes substantially collimated; that is, it is comprised of substantially parallel rays 22, 24 which exhibit small angles of divergence from a focal point or convergence toward a focal point. (The divergence shown in FIG. 1a is exaggerated for clarity of illustration.) The collicators 12 and 14 may not be necessary when the light source 10 produces a low divergence light beam. This is often the case where the light source comprises a laser. The geometric configuration of region 26 may also function to further collimate the light beam 18. Light scattered from the sample within region 26 is detected and analyzed by analysis channels 16a through 16h. Channels 16 are positioned adjacent to and along the longitudinal axes 20, 28 of the light beam 18 and sampling region 26, respectively. Analysis channels 16 collect scattered light from region 26 from either side of axis 28, as illustrated by channels 16a, 16b, 16e, 16f, 16g and 16h, or from both sides as illustrated by channel 16c. Light scattered toward the side of the axes 28 opposite channel 16c is collected and reflected back to channel 16c by a mirror 16d. Mirror 16d may be either a planar mirror or a focusing mirror.

In one embodiment utilizing the collimated beam system 2, the light beam 18 is polarized. The direction of polarization of the E-vector is along the Y-axis which, in reference to FIG. 1a, is the axis perpendicular to the plane of the figure. The direction of propagation of light beam 18 is along the Z-axis, and the detector channels are substantially aligned with the X-axis and lie in the XZ plane.

Figure 1B:
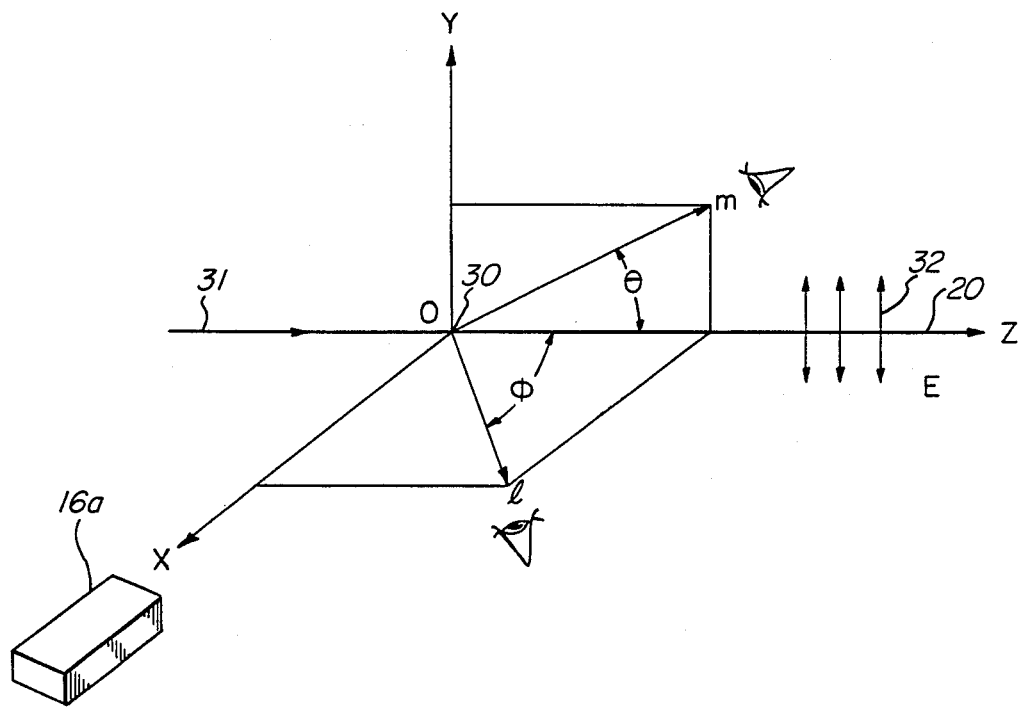
FIG. 1b is a three-dimensional coordinate system diagram showing the scattering geometry for the utilization of polarized laser light in a Raman spectrometer.

The scattering geometry for polarized light Raman scattering is illustrated in FIG. 1b. The scattering sample is located at the origin, 30 of the XYZ coordinate system and is illuminated by polarized light 31 propagating along the Z-axis 20. The E-vector polarization state 32 of the polarized light 31 is in the YZ-pane. The scattering properties of the Raman light scattered into the two orthogonal planes (planes YZ and XZ) which are parallel to the Z-axis of propagation are of particular interest in this geometry.

Raman scattered light consists of isotropic and non-isotropic components. The resulting scattering intensity distribution in space can be described in terms of the invariant, a, which is a measure of the average polarizability, the anisotropy of the polarizability, $\gamma^2$, and the angle in the observation plane. In the XZ plane, a general observation direction indicated by the vector ol makes an angle $\phi$ with the Z-axis. In the YZ plane, a general observation direction indicated by the vector Om makes an angle $\theta$ with the Z-axis. In an assembly of N randomly-oriented molecules in a sample irradiated with monochromatic radiation of wave number, $\bar{v}_o$, incident polarization state $p_i$ and irradiance $\tau$, $^{pi}I_{ps}(\theta)$ and $^{pi}I_{ps}(\phi)$ represent the intensities of scattered radiation of polarization state $p_s$ scattered in directions Om and ol, respectively, are given by:

$$^{pi}I_{ps}(\theta) = \frac{\pi^2}{\epsilon_o^2}(\bar{v}_o \pm |\bar{v}_{vf}v_i|)^4 N_{vi} f(a^2, \gamma^2, \delta^2, \theta)\tau \quad (1)$$

$$^{pi}I_{ps}(\phi) = \frac{\pi^2}{\epsilon_o^2}(\bar{v}_o \pm |\bar{v}_{vf}v_i|)^4 N_{vi} f(a^2, \gamma^2, \delta^2, \phi)\tau \quad (2)$$

where $|v_{vf}v_i|$ is the absolute value of the magnitude of the wave number associated with the vibrational transition of $v_f \rightarrow v_i$, and − and + signs refer to Stokes and anti-Stokes Raman scattering, respectively. $Nv_i$ is the number and $f(a^2,$ of modules in the initial vibrational state $v_i \gamma^2, \delta^2, \theta)$ and $f(a^2, \gamma^2, \delta^2, \phi)$ are functions of the invariants $a^2, \gamma^2, \delta^2$ and the observation angles $\theta$ and $\phi$.

Where $^\perp I(\phi)$ is the Raman scatter intensity as a function of $\phi$ in the XZ plane which is perpendicular to the polarization E-vector, and $^\parallel I(\theta)$ is the Raman scatter intensity as a function of $\theta$ in the YZ plane which is parallel to the polarization E-vector, then $$^\perp I(\phi) = {^\perp I}_\parallel(\phi) + {^\perp I}_\perp(\phi) \quad (3)$$

$$^\parallel I(\theta) = {^\parallel I}_\parallel(\theta) + {^\parallel I}_\perp(\theta) \quad (4)$$

Then from D. A. Long, *Raman Spectroscopy*, McGraw-Hill, 1977, pages CRS6–CRS7:

$$^\perp I(\phi) = a^2 + \frac{7\gamma^2}{45} \quad (5)$$

$$^\parallel I(\theta) = a^2\cos^2\theta + \frac{\gamma^2(6 + \cos^2\theta)}{45} \quad (6)$$

Equation (5) indicates that the Raman scattering intensity is isotropic in the plane perpendicular to the E-vector (XZ plane). In other words, $^\perp I(\phi)$ is not functionally dependent upon the angle $\phi$ in the XZ plane. Equation (6), on the other hand, indicates a non-isotropic $\cos^2\theta$ variation in the Raman scattered signal intensity in the YZ plane, which is parallel to the E-vector of the radiation. That is, for any given value of $\phi$, there will be a $\cos^2\theta$ variation in Raman signal intensity for any of an infinite number of planes parallel to the electric E-vector which also pass through the point 30. Therefore, the maximum Raman scattered signal in the YZ plane occurs when $\theta=0$. At $\theta=\pi/2$, the Raman scattered intensity is at a minimum, but generally non-zero, value. The spatial Raman scattering intensity distribution is given by the sum of Equations (5) and (6) and reaches a maximum in the XZ plane ($\theta=0$).

It is noted that when $\theta=0$, $\phi$ may be varied from 0° to 360° without changing the Raman scattered intensity; however, as $\phi$ approaches 0 and $\pi$, the incident laser light intensity and the Rayleigh scatter intensity greatly overwhelm the Raman signal.

From the above, it is apparent that to optimally collect the scattered Raman light, it is preferable to locate each analysis channel 16 so that it collects Raman light in the XZ plane. A particularly convenient direction in the XZ plane is in the direction of the X axis, which is perpendicular to the laser beam axis 20 and the electric E-vector axis 32. It will be readily apparent to one skilled in the art that there are numerous ways to achieve this desired alignment. The techniques described herein are thus meant to be illustrative but not limiting.

In the embodiment 4 of the invention utilizing a focused beam, as shown in FIG. 1c, plural high intensity regions 36 or focal points are formed along the longitudinal beam axis 20. The focal points 36 are formed by passing beam 18 from source 10 through optical lenses 38 or other equivalent focusing means. The analysis channels 40 are positioned to sample Raman scattered light from samples located at these high intensity regions 36. Analysis channels may be located in any position about the axis 20 as shown by channels 40a, 40d and 40e. Raman scattered light may be collected from opposing sides of the axis 20 by using a collection mirror 40c in conjunction with a channel 40b located opposite the mirror 40c. Alternatively, an array of channels 40f may be located in an equatorial plane 42 about the axis 20 and high intensity region 36d. When using the equatorial array 40f, it may be desirable for the incident beam 18 to be unpolarized.

These and other methods for the placement of the analysis channels 40 about a region of a high intensity 36 will be apparent to one skilled in the art. In particular, D. A. Long, *Raman Spectroscopy*, supra, pp. 132–135, describes an analysis channel position which collects light from a focused laser beam. Herchel, et al., in an article entitled "An Efficient Intracavity Laser Raman Spectrometer," *Applied Spectroscopy*, Vol. 32, No. 3, 1978, discusses Raman scattering at a focused location of a laser beam. Albrecht, et al., in German Pat. No. De. 27 23 939 C2 (1983), discusses an array of analysis channels in an equatorial plane about a high intensity or focused region.

Figure 2:
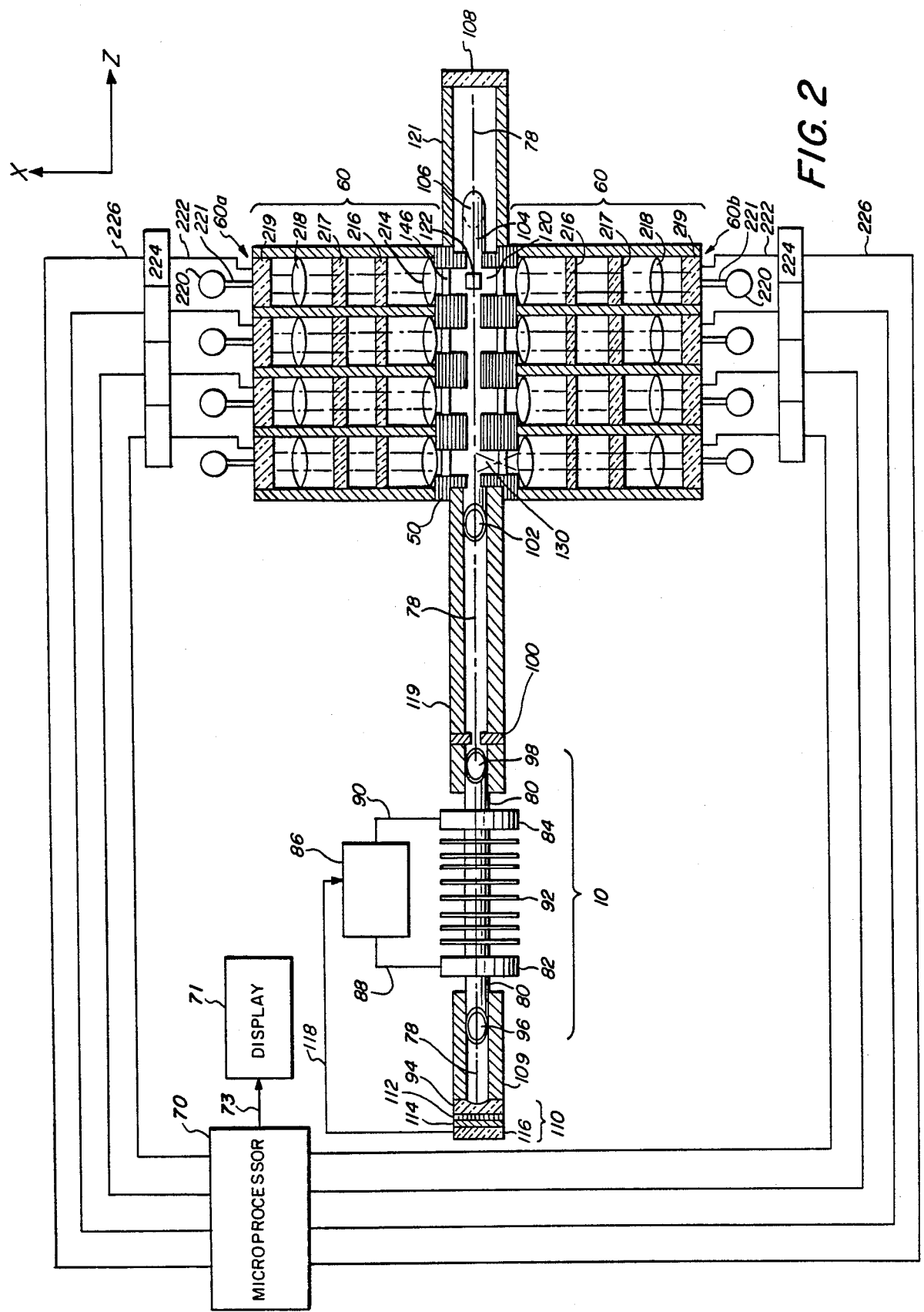
FIG. 2 is a top view schematic diagram showing a complete and preferred embodiment of a laser-activated Raman scattering, sampling and multi-channel detection system using an intracavity gas cell and collimated laser beam.

An embodiment of the invention incorporating the collimated beam geometry is illustrated in FIG. 2. This system broadly comprises a source of polarized laser radiation 10 which is connected at one end to the gas cell 50. An array of detector channels 60 are positioned adjacent the gas cell 50. A microprocessor 70 is connected to the detectors 60. In operation, laser 10 produces a collimated beam of polarized optical radiation 78 which propagates into the gas cell 50 and scatters from a gas sample contained in the gas cell. The Raman scattered radiation which, as explained above, is emitted nonisotropically is collected over as large a solid angle as possible by a series of detector channels 60 which are located approximately perpendicular to and on either side of the axis of the cylinder formed by the incident laser light. The Raman signals are analyzed with a microprocessor 70. Based on the analysis of the Raman scattered light signals, microprocessor 70 reports the identity and concentration of up to eight specific gases which may comprise the gas sample.

LASER SOURCE

The laser 10 is preferably a continuous wave argon ion laser capable of producing a polarized beam of light 78 having a wavelength of 488 nanometers. Laser 10 comprises a plasma discharge tube 80, a cathode 82 located near one end of the discharge tube 80 and an anode 84 located near the opposite end of the discharge tube 80. A power supply 86 is connected to the cathode 82 and anode 84 by lines 88 and 90, respectively. A radiator or heat exchanger 92 thermally contacts and surrounds a portion of the discharge tube 80 located between the cathode 82 and anode 84. A lasing gas mixture containing argon gas is confined within the plasma discharge tube 80.

Power supply 86 supplies a high voltage between the cathode 82 and anode 84 thus creating a plasma discharge through the lasing gas mixture within the plasma discharge tube 80. Argon atoms contained in the gas mixture are exited to higher energy levels and when properly stimulated simultaneously de-excite to a lower energy level, thus generating laser emission of light at specific characteristic wavelengths. One such wavelength characteristic of argon is 488 nanometers. For optimum light amplification to occur, the emitted light must propagate through a resonant cavity, thus stimulating further emission of additional excited atoms of argon.

A laser source 10 having the above-described characteristics is readily available from Ion Laser Technology Corporation located in Salt Lake City, Utah as Model No 350A. The extra cavity power of the beam from this laser, when using a 98 percent reflectance output coupler 94, is preferably on the order of tens of milliwatts.

The resonant cavity for the embodiment shown in FIG. 2 encompasses the region extending from the output coupler reflector 94 opposite the cathode 82 portion of the discharge tube 80 to an end reflector 108 opposite the anode 84 portion of the discharge tube 80. Light beam 78 produced by laser source 10 follows an optical path through the resonant cavity which comprises from left to right in FIG. 2 output coupler reflector 94, a first Brewster window 96, the discharge tube 80, a second Brewster window 98, an intracavity aperture 100, a third Brewster window 102, an interior chamber 104 of gas cell 50, a fourth Brewster window 106, and an end reflector 108. Typically, output coupler reflector 94 comprises a high reflectivity curved mirror coated with a multilayer dielectric coating. A dust-tight sleeve 109 surrounds the mirror 94, Brewster window 96 and cathode end of plasma tube 80 to protect these components from particulate and molecular contamination which could adversely affect the optical power circulating in the resonant cavity. Similarly, a dust-tight sleeve 199 surrounds the anode end of plasma tube 80, Brewster window 98, intracavity aperture 100 and Brewster window 102 on gas cell 50, to protect this portion of the resonant cavity from contamination. A third dust-tight sleeve 121 protects Brewster window 106 on gas cell 50 and end reflector 108. End reflector 108 comprises a high relectivity mirror coated on the back side of a Littrow prism. Alternatively, end reflector 108 may comprise a flat mirror with a laser line selective coating. In this case, the output coupler 94 would also be coated with a laser line selective coating for wavelength selection. Brewster windows 96, 98, 102, 106 and end reflectors 94, 108 and their respective coating and/or orientations are selected to maximize the power of the polarized selected wavelength light circulating in the resonant cavity. Additionally, the Brewster windows 96, 98, 102, and 106 are oriented to cause laser beam 78 to have a polarization vector that is substantially perpendicular to the plane of FIG. 2.

The position of gas cell 50 and plasma tube 80 are within the resonant cavity of the laser. This configuration is often referred to as intracavity. Location of the gas cell 50 within the resonant cavity increases the amount of laser power available for Raman scattering from the gas molecules in the cell chamber 104. The intracavity power is higher than extracavity power by a factor of $[1+R]/T$, where R and T are the reflectivity and transmission, respectively of output coupler reflector 94. Since there is no need to extract substantial quantities of laser light from the resonant cavity when using an intracavity cell 50, both the end reflector 108 and the output reflector 94 may have a reflectivity of approximately 99.9% or greater, thus providing a substantial increase in circulating optical power and Raman scatter signals for intracavity sample placement as compared with extracavity placement.

Stabilization of laser beam 78 is provided by a beam analysis system 110 comprising output coupler reflector 94, a narrow laser line filter 112, a diffuser 114, and a light detector 116. Filter 112 is located adjacent output coupler reflector 94 and diffuser 114 is located between filter 112 and detector 116. Detector 116 is connected via line 118 to laser power supply 86. Filter 112 serves to reject diffuse Argon plasma glow and transmit the small amount of laser light which transmits the output coupler mirror 94.

Stabilization is achieved by monitoring the intensity of light beam 78 via detector 116 and adjusting the power supply 86 in response to changes in the intensity of the light beam 78, thus forming a feedback system. A small sample, approximately 0.1% of light beam 78 is extracted from the resonant cavity via output coupler reflector 94, which is selected to have a reflectivity of approximately 99.9% or greater. Filter 112 allows light having a wavelength of substantially 488 nanometers to pass to diffuser 114. Diffuser 114 causes the sampled and filtered 488 nanometer light sample to be spread over a substantial portion of the sensitive region of detector 116, thus reducing effects of beam wander over the detector's sensitive region which may not be uniform. The output from detector 116, which is a function of the sampled light beam intensity, is used to control the output from power supply 86 to the plasma discharge tube 80, thus completing the feedback loop for stabilizing the intensity of the laser beam 78.

In order to provide a substantially collimated light beam 78 within gas cell chamber 104, the focusing output coupler reflector 94 is located at the end of the resonant cavity furthest from the gas cell 50. The flat end reflector 108 further serves to preserve a narrow essentially collimated beam 78 within gas cell 50. In addition, the bore diameter of the plasma tube 80 (approximately 0.050 inches) serves as an effective aperture which further serves to shape the laser beam and collimate it in the gas cell. In addition, intracavity aperture 100 is placed close to the discharge tube 80 and about 3 inches from gas cell 50 to effectively reduce plasma tube collateral radiation from reaching the gas cell interior. In this arrangement of optical elements, no focusing elements are located near the chamber 104 of gas cell 50, thus improving the collimation of light within the chamber.

The above-described laser system thus provides a substantially collimated, polarized, high intensity, intracavity beam 78 of 488 nanometer light within the chamber 104 of has cell 50.

GAS SAMPLE CELL

Gas cell 50 provides a containment used for the gas sample being analyzed which enables the sample to be placed within the resonant cavity of the laser without substantially reducing the circulating optical power in the cavity. This arrangement makes efficient use of available laser output power by maximizing the number of interactions between the laser beam and the gas molecules which result in Raman scattering. As shown in both FIGS. 2, and 3, a preferred embodiment of gas cell 50 comprises a central chamber 104 and eight output channels 120 which form optical passageways between the central chamber 104 and the outside of the gas cell. The eight output channels are arranged so that they are perpendicular to a longitudinal axis 121 of the chamber 104 which coincides with the axis of propagation of the laser beam 78. The output channels 120 further have axes of symmetry located in the XZ plane of FIG. 2, which is the plane perpendicular to the E vector axis of polarization of the laser light beam 78.

One embodiment of a gas sampling cell 50 is shown in detail in FIGS. 3a, 3b, 3c, and 3d, and comprises a framework 140 having a hollow interior 104, passageways 142, 144 for bringing a gas sample into and out of the interior, and output channels 120 through which Raman scattered light may pass. The axis 121 of interior chamber 104 is oriented to accommodate the passage of the laser beam 78 through the axial center of the chamber 104. In one embodiment, the chamber forms a hollow cylinder having a diameter of approximately 0.125 inches, however, other shapes and sizes may also be used. The volume of the chamber is selected to be as small as possible so that response time is fast, but still large enough to provide an adequate volume of gas for analysis. Additionally, the bore size of the chamber should be selected so that a substantial percentage of the laser beam power can interact with the gas sample. A preferred chamber shape also eliminates as much as possible dead air spaces where portions of the gas sample could collect inside the chamber. At either end of the housing 140 are mounted Brewster windows 102 and 106 (shown in FIG. 2). The purpose of Brewster windows 102 and 106 is three-fold; first, they constrain the sample gas within chamber 104 and thus minimize sample volume which reduces response time, second, they serve to maintain the circulating intracavity power of laser beam 78 within chamber 104 and, third, they protect the other optical components in the resonant cavity from possible contamination arising from the gas sample.

As shown in FIGS. 2 and 3a, the gas cell 50 also contains opposing optical side windows 146 on either side thereof. Side windows 146 can be continuous along the side of the cell housing 140 or can be a series of windows 146 mounted in channels 120 in the cell housing walls, as illustrated. Side windows 146 are preferably mounted parallel to the longitudinal axis 121 of housing 140 and laser beam 78 to provide for optimal passage of scattered light signals from the polarized laser beam 78 to the output channels 120. Since the windows 146 must transmit the Raman scattered light to a detector, they must pass the desired wavelengths. Hence, a high efficiency broadband anti-reflection coating is appropriate. Broadband coatings are typically formed of multilayer dielectric films, comprising alternate layers of various refractive index transparent materials, combined in such a way so as to reduce the overall reflectance to an extremely low level for the spectral range covered. Over the broadband range, the reflectance will not generally exceed 1.0% and will generally be below 0.6%.

Side windows 146 may be any material which can constrain the gas sample and still transmit the Raman scattered light. The windows may be planar, as depicted in FIGS. 1, 2, and 3a. Alternatively, the collection optics 214 shown in FIG. 2 could be used for the side windows 146 as long as the focal length of the lenses 214 coincides with the optical center of the laser beam 78. Side windows of any alternative configuration may also be coated with a V-band multiplayer dielectric coating to reject elastically-scattered laser light.

Figure 4:
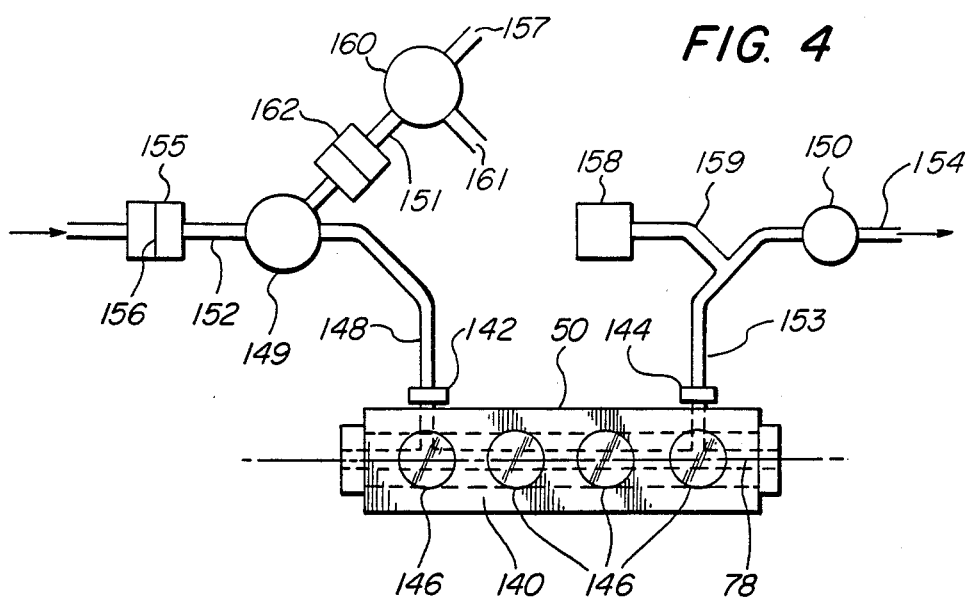
FIG. 4 is a schematic diagram showing the flow of gas into and out of the gas cell.

As shown in FIG. 4, the gas cell 50 is connected to the source of gas to be analyzed by an inlet 142. An outlet 144 is provided for discharging the sample gas from the cell chamber 104. The design of the cell 50 allows for a very small volume of gas, typically between about 0.1 and 1.0 cubic centimeters, to continuously flow through the laser beam 78. The cell 50 is also well adapted for use in a batch-type operation in that only a small sample is required of any given gas to be analyzed. The inlet 142 is connected via supply line 148 to a three-way solenoid valve 149. Sample gas is drawn into the cell interior 104 by means of an air pump 150 which is connected via a tubing line 153 to outlet 144. Depending upon the input position of the solenoid 149, which is attached to input lines 151 and 152, a variety of sources may supply gas samples to the cell 50. Line 151 connects to a second three-way solenoid valve 160 which, when not activated allows room air to be drawn via line 161 into the cell 50 for system calibration against nitrogen and oxygen gas, or when solenoid 160 is activated a calibration gas mixture may be drawn into the cell 50 via line 157. Alternatively, a respiratory gas or other sample gas may be drawn vial line 152 from the airway of a patient or other sample source. A filter housing 155 containing a membrane filter 156 is located in line 152 upstream of solenoid 149 to remove unwanted particulate matter from the sample when sampling from a patient's airway to minimize end and side window contamination in the cell 50. A second filter 162 may also be used to prevent contamination of cell 50 from calibration gases. Tubing 153, connected to cell outlet 144, conveys sampled gas out of the cell 50 to the pump 150. Tubing 154, connected to pump 150, conveys sampled gas from the pump for disposal or re-introduction into a patient's airway or for collection and storage. Electronic barometer 158 is connected to sample line 153 via sample tube 159 and functions as a monitor of gas pressure in the interior of sample cell 50. If membrane filter 156 becomes plugged, the gas pressure in the sample cell 50 will drop below a threshold value causing measured signals to be erroneous. In such case, the electronic barometer 158 signals the microprocessor 70 which, in turn, alerts the user or operator.

Referring again to FIG. 2, gas cell 50 can be easily removed from the intracavity space by sliding sleeve 119 along the plasma tube 80 away from gas cell 50. The cell is then slide away from sleeve 121 and lifted out of the resonant cavity. Easy removal of the gas cell 50 facilitates field service and maintenance. For example, cleaning of the end windows 102 and 106 may be required if they become contaminated by dust particulates or organic films.

MULTIPLE DETECTOR CHANNELS

As shown in FIG. 2, Raman scattered light exits the gas cell 50 through windows 146 and enters the array of detector channels 60. The detector array 60 shown in the embodiment of FIG. 2 comprises a series of eight individual detection channels on either side of gas cell 50, one channel being located to detect the light output from each of the eight output windows 146 of the gas cell 50. The eight detector channels are all quite similar, therefore, for clarity, only one channel will be described in detail, it being understood that the explanation also applies to the remaining seven channels. The choice of eight channels is illustrative only, it being understood that a different number of channels may be aligned on either side of the gas cell depending upon the number of gases being sampled and detected.

A typical detector channel 60a comprises an input collection lens 214 positioned to receive light from a region 122 located within the chamber 104 through the window 146. One or more serially oriented high rejection laser line filters 216 are positioned downstream from lens 214. A narrow bandwidth interference filter 217 is located adjacent filter 216 and an output lens 218 is positioned adjacent filter 217. Depending upon the type of detector used, lens 217 may or may not be required. In one embodiment, both collection lens 214 and output focusing lens 218 are plano convex borosilicate lenses, however, other suitable lens shapes and materials may also be used. A preferred embodiment utilizes a photomultiplier tube (PMT) 219 to detect light from the cell after passing through lens 214, filters 216 and 217, thus eliminating lens 218. The PMT is connected to a power supply 220 via path 221. Electrical pulses representative of light detected by the PMT 219 are transmitted via a line 222 to an amplifier discriminator 224 where they are processed and analyzed. the processed pulses are then transmitted to microprocessor 70 via lines 226 where they are accumulated, analyzed, stored and displayed on display 71.

Alternatively, detector 219 may be any suitable detector utilizing photon counting or photocurrent electronics, such as a photodiode, intensified diode array, charged coupled device or photomultiplier tube power by an appropriate power supply 220 via line 221.

Figure 5:
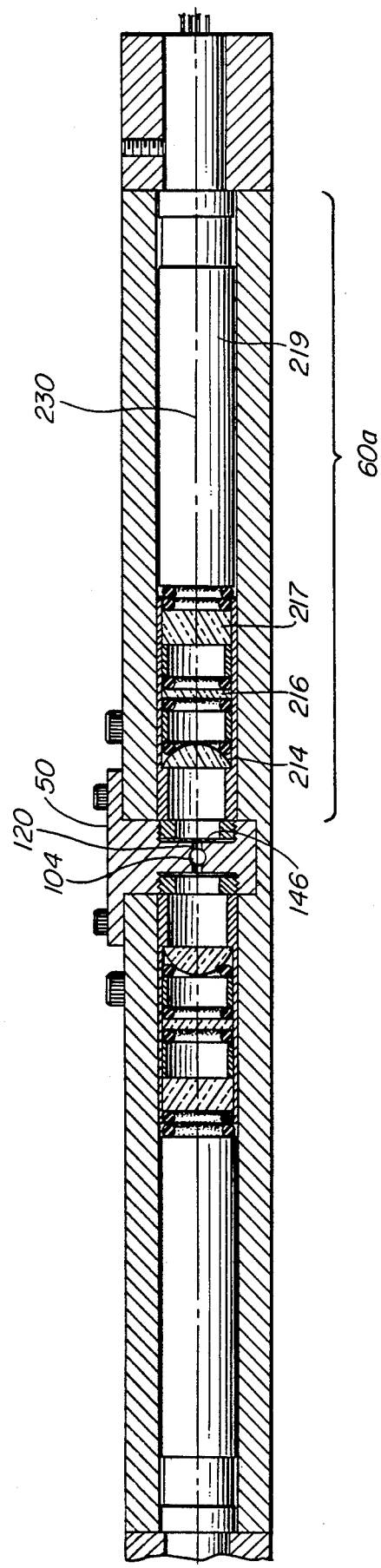
FIG. 5 is a cross-section view of a preferred embodiment of the detector channels shown in position adjacent the gas cell.

A more detailed cross-section view of a typical detector channel 60a is shown in FIG. 5. The detector 60a is positioned against the gas cell 50 so that the optical axis 230 of the detector channel 60a is perpendicular to the axis of propagation of laser beam 78 as well as being perpendicular to the direction of polarization of the E-vector of the laser beam. In FIGS. 1b and 2 this direction is along the x-axis. Raman scattered light from region 122 of the chamber 104 is transmitted through window 146, collected and collimated by lens 214, filtered by the laser line rejection filter 216 and the Raman line bandpass filter 217 before being detected by PMT 219. Lens 218 serves two functions. First, it collects Raman scattered light. Second, it collimates this light so that when it travels through the filters 216 and 217, the filters function optimally to reject elastic scatter and transmit specific Raman scattered light. Collection lens 214 may actually be a series of optimally configured lens elements all of which are anti-reflection coated. One such example is a fast (f/1.2) camera lens. Each collection lens 214 must be properly aligned with respect ot the laser beam 78, to ensure efficient collection of the scattered light from the gas cell 50. Elastically and inelastically-scattered light collected by lens 214 in each channel 60 is directed to one or more serially-oriented high rejection laser line filter(s) 216. Filter(s) 216 greatly attenuates the elastically-scattered laser line (Rayleigh scatter) to minimize interference with the Raman or inelastically-scattered light and transmits substantially all of the inelastically-scattered Raman lines. The transmitted Raman lines which arise from the incident laser beam interacting with the sample gas correspond to the vibrational/rotational energies of the scattering molecules are then transmitted through interference filter 217.

The filter portion is designed to reject elastically-scattered laser light and all Raman lines except the specific line of interest. This can be accomplished by the use of two filters. However, there are commercially available filter designs in which one filter performs the same functions as the serial arrangement of the two filters 216 and 217. Filter 216 is a high rejection laser line filter which greatly attenuates the elastically-scattered laser line to minimize interference in the Raman scattered light while allowing all wavelengths of the Raman scattered light to be transmitted through the filter. Filter 217 is a specifically chosen interference filter which rejects all Rayleigh and Raman scattered light wavelengths except the desired one. If desired, filters 216 and 217 could be in reverse order, with filter 217 being positioned between lens 214 and laser line filter 216.

The Raman spectra line-specific filters 217 may be different in each channel and are chosen so that instrument can detect and quantify a number of different polyatomic gas of interest. Hence, the number of channels to be utilized is dependent upon the number of gases to be identified and quantitated.

The collimated beam embodiment of the invention illustrated in FIGS. 1a and 2 collects light from a narrow rectangular-shaped area 122 within the gas cell 50. For example, see output channels 120b in FIG. 3. Thus, an ideal optical system would comprise a lens system having a rectangular shaped focal spot and would collimate the light collected from the chamber 104 for further propagation through filters 217 and 218. This is desirable because multilayer dielectric filters which are designed to reject elastically scattered laser light and transmit specific Raman lines function best when the incident light is reasonably well colimated. Such a special purpose lens is difficult to produce and expensive.

Alternatively, one approach for implementing the collimated beam embodiment of the invention utilizes a single plano-convex collection lens 214 to collect signals from as wide an interception angle of laser beam 78 in gas cell 50 as is possible. In practical application, light collection is from the rectangular-shaped region 122 of the laser beam having dimensions of about 0.5 mm in width and several millimeters in length. The result is that the lens 214 collects much more light (both elastic and inelastic) than if it were viewing a point source within the laser beam 78. Consequently, the Raman signals are much higher. However, because light collection is from an extended source, some of the collected light is incident upon the filters 216 and 217 non-normally (i.e., not perfectly collimated), resulting in non-zero levels of stray light background signal being transmitted to the detector 219. Thus, the Raman signals are relatively high but the signal to stray light background ratio is relatively low. Typical values of this ratio are 230:1 for $CO_2$ and 7:1 for 5% Halothane. It has been found that the advantages resulting from the higher Raman signal levels dominate the compromise and make the higher signal to background levels acceptable.

In tests conducted on an instrument designed in accordance with the invention described, the detected signal levels for the molecules $N_2$, $O_2$, $CO_2$ and $N_2O$ ranged from approximately 20,000 to approximately 100,000 counts per second for pure gases using point source collection via an iris diaphragm and approximately 50,000 to 250,000 counts per second for collection from the entire laser beam 0.5 mm diameter × 4 mm long in the gas cell. The corresponding stray light scatter backgrounds from elastic scatter of the Rayleigh line were determined for these two collection geometries using pure argon and were found to be approximately 500 and 1,000 counts per second, respectively.

If desired, certain refinements may be made in gas cell 50 and in the optical filter-detector channels 60 to reduce stray scattered laser light and minimize background noise. For example, the aperture size for the laser beam path entering and exiting the gas cell along its longitudinal axis may be determined by an iris or circular baffle (not shown) located at either or both ends of the cell 50 just inside the end windows 102 and 104. Similarly, an iris or baffle (not shown) or series of baffles may be located in the channel between each side window 146 and the corresponding collection lens 214. Additional baffles (not shown) may be positioned between the collection lens 214, filters 216 and 217, and between focusing optics 218 and photodetector 219 to minimize stray light. Also, as shown in FIG. 2, intracavity aperture 100 functions to reduce the collateral plasma glow contribution to the background signal. In addition, flat black paint may be used to coat the interior surface of the optical collection channels 60 to further absorb stray light background.

The collection lens 214 may be replaced by a single or optimally arrayed series of fiber optics. Such fiber opticals generally have a much higher numerical aperture than lenses and are therefore more efficient light collectors. After the collection of the Raman scattered light, any means of transmitting or redirecting the signal to the optical filter system and/or detectors may be utilized, i.e., refractive optics such as lenses, reflective optics such as mirrors or transmissive optics such as fiber optics.

Since scattering from polyatomic gaseous molecules causes a frequency shift from that of the incident radiation by an amount corresponding to the vibrational/rotational energies of those molecules and is species-specific, an analysis of the frequency components present in the Raman scattered light provides identification and quantification of the gases present in the scattering volume. Quantification is determined from the measure intensities of the Raman signals calibrated against reference gases and known Raman scattering cross sections.

In order to quantify each gas species, the narrow bandwidth interference filter 217 is selected to transmit the wavelength of the Raman line for that gas. As shown in FIGS. 2 and 5, these filters are represented by a specific multilayer dielectric interference filters 217 located in each channel 60. each specific filter 217 is chosen to pass along one or more Raman scattered lines which correspond to a discrete molecular species. A different filter is utilized for each channel, thereby making each channel specific to the detection of a different polyatomic gas species. It is possible to utilize filters which transmit more than one discrete Raman line for gas quantification. A case in point is the C-H stretch lines for the anesthetic gases with Raman frequency shifts in the region of 2900 cm$^{-1}$ to 3100 cm$^{-1}$. It is also possible to utilize data from two or more channels to identify the type of anesthetic agent in use.

Since primary interest of this invention is focused on analysis of respiratory and anesthetic agent gases, the following table illustrates the Stokes Raman frequency shifts and relative scattering cross sections for several representative gases of interest. The Raman spectra for the anesthetic agents is very complex. Therefore, the frequency shifts shown in TABLE I for the anesthetic agents are the ones selected empirically for use in a preferred embodiment. Relative scattering cross sections for the anesthetic gases and C-H stretch are also not readily available due to the complexity of the spectra.

TABLE I

Frequency Shift and Normalized Relative Scattering Cross Section for Several Respiratory and Anesthetic Gases

| Gas Species | Frequency Shift (CM$^{-1}$) | Relative Scattering Cross Section |
|---|---|---|
| $N_2$ | 2331 | 1.0 |
| $O_2$ | 1555 | 1.0 |
| $CO_2$ | 2143 | 0.9 |
| CO | 1285 | 0.8 |
|  | 1388 | 1.2 |
| $N_2O$ | 1285 | 1.8 |
|  | 2224 | 0.5 |
| $H_2O$ | 3652 | 2.8 |
| Isoflurane | 995 | — |
| Enflurane | 815 | — |
| Halothane | 717 | — |

In a detection channel 60 for a specific gas species, the Raman scattered light having the selected frequency passes through interference filter 217 in each channel and is input to a separate detector 219. Optional focusing lens 218 may be used for some filters and detectors. The detector 219 can be any device capable of receiving the optical signal, and amplifying and processing it into useful data. Represented in FIGS. 2 and 5 is a photomultiplier tube (PMT) 219 which is connected to a signal processing unit 224 which may be a photon counter, a photocurrent amplifier or other device including a central processing unit or microprocessor which can further amplify, process and quantitate the Raman signal into useful analog or digital data which is then displayed on display device 71, e.g., a digital display, a CRT screen and/or printer. Table I shows that those gases of interest generally have frequency shifts substantially smaller than that for water vapor. Therefore, Raman signals from water vapor do not interfere with the Raman signals of interest since there is rarely any significant spectral overlap between the Raman signals. This is true provided that narrow (1 nm full width half maximum) bandpass interference filters with high (>1,000) out-of-band rejection are used.

In a preferred embodiment for the identification and quantitation of anesthetic agents and respiratory gases, eight multilayer dielectric filters 217 are used. Anesthetic agents halothane, enflurane, and isoflurane are detected by filters 217 having center wavelengths of 505.7 nm, 508.2 nm and 512.9 nm, respectively. Carbon dioxide, oxygen, nitrous oxide and nitrogen are quantitated by filters 217 having center wavelengths of 523.5 nm, 528.1 nm, 547.4 nm and 550.6 nm, respectively. All of the above filters have half bandwidths of approximately 1 nm. The anesthetic agents are quantitated by a filter 217 having a center wavelength of 572.6 nm and half bandwidth of 10 nm. These filters are appropriate for the Raman scattering of the argon laser line at 488 nm.

DATA PROCESSING

Referring again to FIG. 2, the photons received by detectors 219, which are powered by power supply sources 220, are converted to electric current or voltage, amplified and sent by signal line 226 as photocurrent or photo voltage to a pulse amplifier-discriminator or current or voltage amplifier circuit 224. These signals are converted into standard digital pulses and relayed to microprocessor 70 via signal lines 226. The processing of the specific Raman lines entering detector 219 into useful data is accomplished by known means, and the signals entering microprocessor 70 may be processed by software to provide the desired data which are then sent to a digital or analog CRT display 71 via line 73.

While state of the art techniques are used to process the data, the manner in which the data are collected, processed and displayed may be varied to provide for the needs of the end user.

The primary functions of microprocessor 70 are to accumulate, analyze, store, and display the date received from collection channels 60. Secondary functions may include routine monitoring of gas flow in the gas cell, laser intensity output, temperatures throughout the system, etc.

Figure 6:
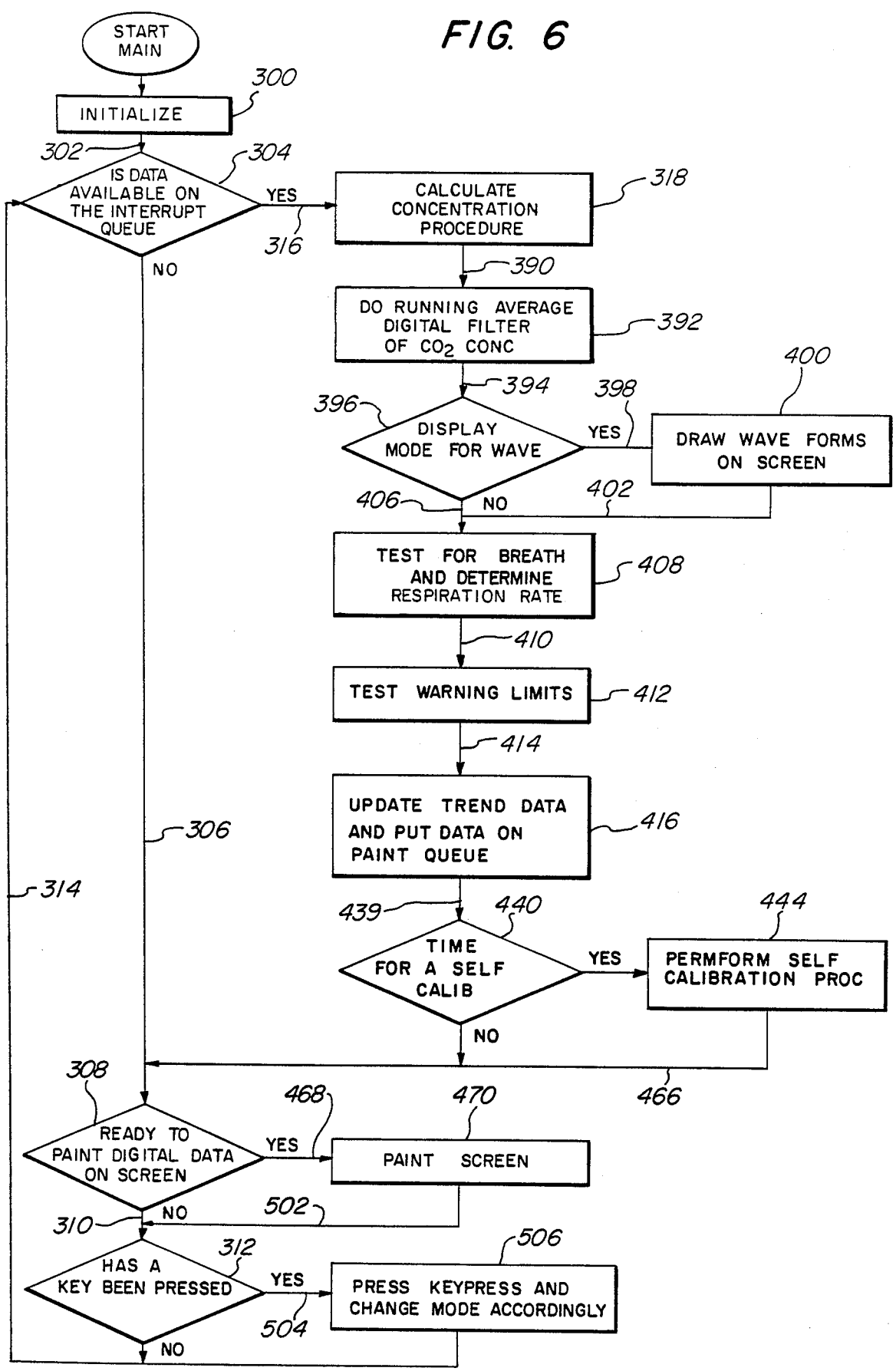
FIG. 6 is a flowchart for the main microprocessor routine for analysis of respiratory gases and anesthetic agents.

The general functions of the microprocessor 70 in a preferred embodiment application for monitoring respiratory gases and anesthetic agents are shown by the flow chart in FIG. 6. On power up of the microprocessor, the software initializes the hardware, sets up the interrupt structure of the program, and sets the global variables to their starting values. It waits for the laser to come on and then displays a starting option screen that allows the user to set or change flags in global variables. One menu option begins execution of the main program. These activities are indicated in activity block 300. Upon receipt of the command to begin operation, the main program software executes in an infinite loop comprising decision blocks and pathways 304, 306, 308, 310, 312, and 314. Within this loop, data is handled as it becomes available until a standby key press is detected in decision block 312 which halts execution of the program and returns control to the starting option screen displayed as part of activity block 300.

A microprocessor timer channel provides a 100 ms strobe to signal the system that data from collection channels 60 are ready for acceptance by the microprocessor. The strobe generates an interrupt, the detector channels are read and the data are made globally available in a queue data structure, for processing as CPU time becomes available. These activities are carried out within decision block 304.

If no data is available on the interrupt queue, control passes via path 306 and the infinite loop continues. If data is available on the interrupt queue, control passes via path 316 to activity block 318 which executes a procedure for calculating concentrations. Details of the activities performed within block 318 are shown in the flow charts of FIGS. 7a and 7b.

Figure 7A:
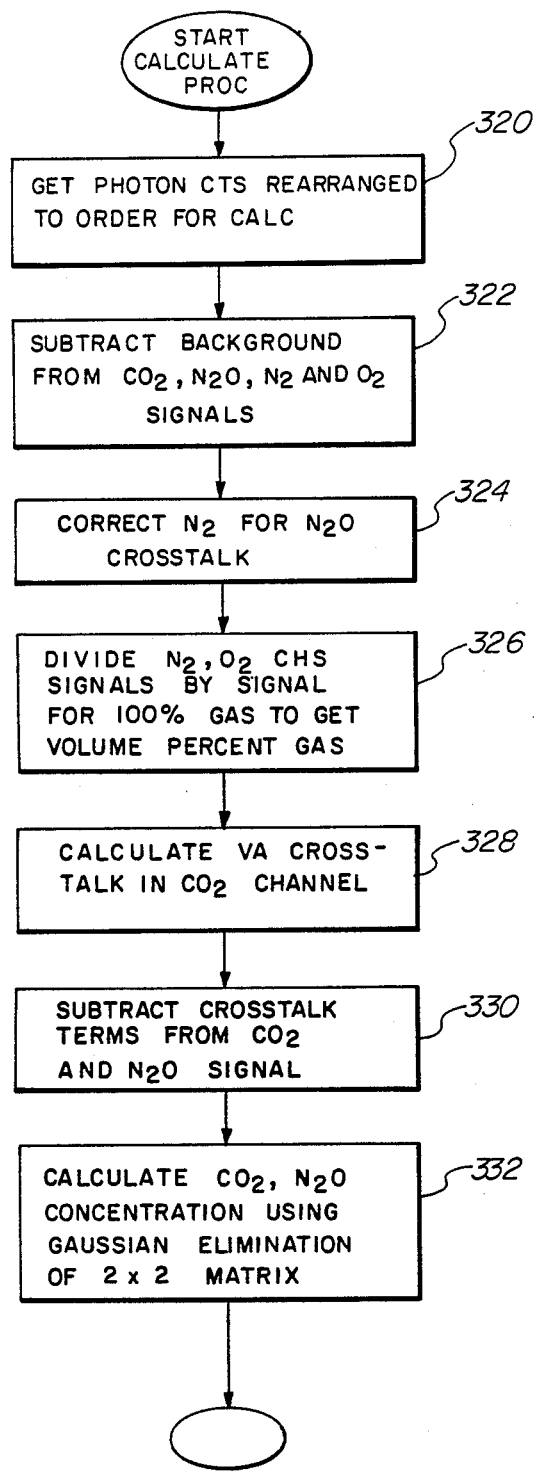
FIG. 7a is a flowchart for the calculation procedure.

The major operation of the calculation procedure, shown in FIG. 7a, is to calculate the volume percent concentration of four gases: oxygen ($O_2$), nitrogen ($N_2$), nitrous oxide ($N_2O$), and carbon dioxide ($CO_2$), as well as one of the three anesthetic vapor agents: isoflurane, halothane, or enflurane.

Oxygen concentration can be calculated directly, as can the anesthetic vapor agent concentration provide that the vapor agent has previously been identified. If the vapor agent has not yet been identified or indicated, the assumption that the vapor agent is isoflurane gives approximately the correct results for enflurane and overestimates the halothane concentration by 100%, but this condition will not continue for more than 20 seconds.

In activity block 322, a background signal level is subtracted from the signals representative of the oxygen, nitrogen, nitrous oxide, and carbon dioxide channels. After the background subtraction in block 322, activity block 324 corrects the nitrogen channel for the crosstalk contribution from nitrous oxide, and then calculates the nitrogen concentration. The nitrous oxide crosstalk contribution is calculated from the previously determined concentration of nitrous oxide. The volume percent gas for nitrogen, and oxygen is determined in activity block 326 by dividing the respective channel signals by a signal representing 100% gas. A crosstalk value for the anesthetic vapor agent in the carbon dioxide channel is then determined in activity block 328 and subtracted from the total signal. Similarly, the crosstalk from nitrogen in the nitrous oxide channel is determined and subtracted from the total signal. After the final subtraction of crosstalk from the carbon dioxide and nitrous oxide signals in activity block 330, activity block 332 calculates the concentration for carbon dioxide and nitrous oxide using a method of solving n equations in n unknowns called Gaussian Elimination. At this point, the flow chart in FIG. 7a connects with the flow chart in FIG. 7b.

Figure 7B:
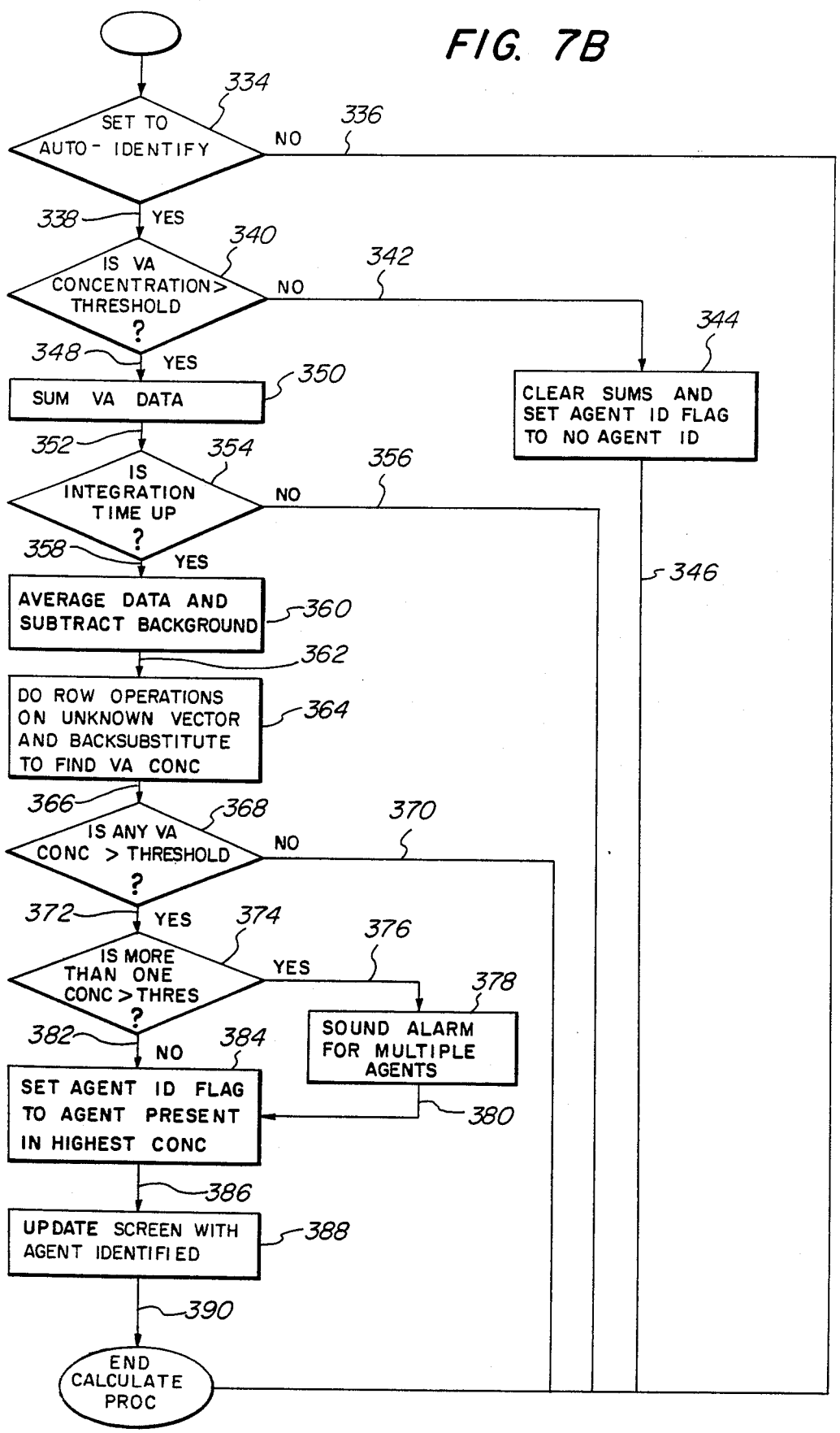

Referring now to FIG. 7b, if the instrument is not set to identify the vapor agent, control is passed from decision block 334 via control path 336 to the end of the calculation routine. If the instrument is set to identify the vapor agent, it will monitor the quantity of anesthetic vapor agent detected in the CH-stretch channel, the channel used to quantitate the anesthetics agents. Control is passed from decision block 334 via path 338 to decision block 340 wherein the concentration of the anesthetic vapor agent is compared to a threshold value. If the vapor agent concentration is less than the threshold, control is passed via path 342 from block 340 to block 344 wherein the sums representing the signals of the various detector channels are cleared and a flag is set which indicates that no anesthetic vapor agent was identified. Control then passes via path 346 to the end of the calculation procedures.

If in decision block 340 the anesthetic vapor agent concentration was found to be greater than the threshold, then control is passed via path 348 to activity block 350 wherein the signals from the three anesthetic filter channels and from the nitrous oxide channel as well as the CH-stretch channel are integrated for a total of 10 seconds.

Control is passed from activity block 350 via path 352 to decision block 354 wherein the duration of the integration time is checked. If the integration time is not sufficient, control passes via path 356 to the end of the calculation procedure. If the integration time is sufficient, control passes from decision block 354 via path 358 to activity block 360 wherein the data are averaged and background is subtracted.

After signal averaging and background subtraction, control passes via path 362 to activity block 364 wherein the data are processed as five equations in four unknowns and the solution is again arrived at using the Gaussian Elimination technique.

The concentrations of the vapor agents determined in activity block 364 are transferred via path 366 to decision block 368. If none of the concentrations of the anesthetic vapor agents are greater than a threshold, then control is transferred via path 370 to the end of the calculation routine. If any of the concentrations of the anesthetic vapor agents are greater than the thresholds, then control is transferred via path 372 to decision block 374. If more than one of the anesthetic vapor agents have concentrations greater than the threshold, then control is transferred via path 376 to activity block 378 wherein an alarm is sounded indicating that multiple vapor agents are present. Control then proceeds via path 380 to activity block 384. If only one anesthetic vapor agent is greater than the threshold in decision block 374, then control is passed via path 382 to activity block 384 wherein an identification flag is set to indicate which anesthetic vapor agent is present in the highest concentration. Control then proceeds via path 386 to activity block 388 wherein the display screen is updated with the identity of the identified vapor agents. Control then passes via path 390 to the end of the calculation routine and proceeds with activity block 392 of the flow chart for the main routine in FIG. 6.

In activity block 392 of the main routine, the $CO_2$ concentration data is filtered using a low pass running average digital filter. Control then passes via path 394 to decision block 396 wherein if the display mode of the instrument is set to show a waveform, control passes via path 398 to decision block 400 which paints the new concentration data point on the display screen. Control then passes via path 402 to activity block 408. If, in decision block 396, the display mode is not enabled, control passes via path 406 to activity block 408 wherein tests are performed to determine whether the patient is exhaling or inhaling. This determination is made by observing whether the carbon dioxide concentration is above a threshold value, which is an indication of expiration. This information is signalled to the rest of the program with a global flag. The number of data strobes between breath detections is measured to supply a respiration rate value. All data are passed via path 410 to decision block 412 wherein all data are compared against upper and lower warning limits as set by the user, and if any concentrations are above the upper warning limits or below the lower warning limits an alarm condition is noted on the display. After checking the warning limits, control passes via path 414 to activity block 416 wherein a procedure which updates the digital data on the screen is executed. A detailed flow chart for this procedure is shown in FIG. 8.

Figure 8:
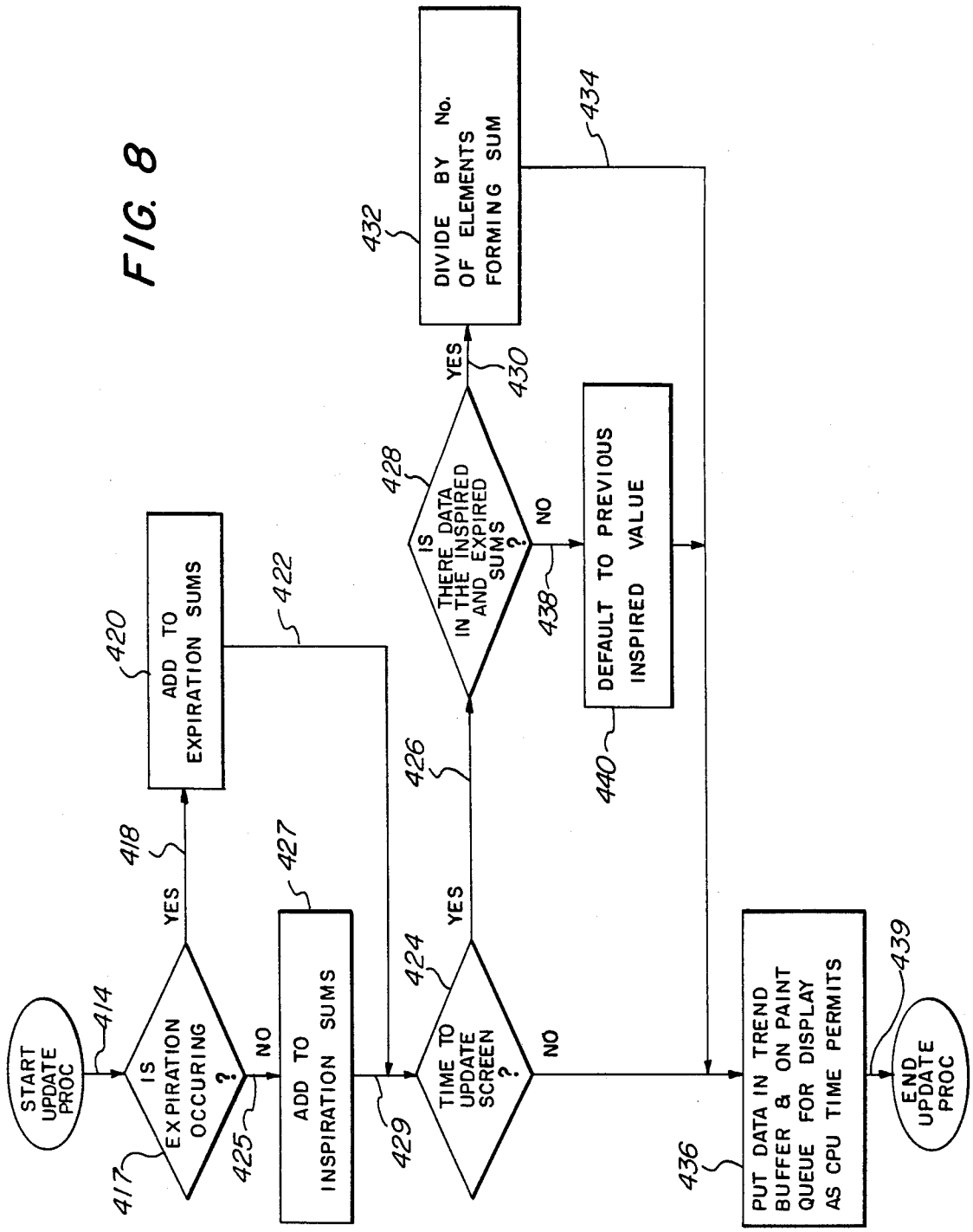
FIG. 8 is a flowchart for the updating of the trend data procedure.

Decision block 417, shown in FIG. 8, determines if expiration is occurring. If expiration is occurring, control passes via path 418 to activity block 420 wherein the current expiration data is added to the expiration data sums. Control then passes via path 422 to decision block 424. If expiration is not occurring at decision block 417, then control is transferred via path 425 to activity block 427 wherein the current data is added to the inspiration sums. Control is then passed via path 429 to decision block 424. If it is time to update the screen for a particular gas, which occurs once every nine seconds, control is passed from decision block 424 via path 426 to decision block 428. If there is data in the inspired and expired sum registers then control passes from decision block 428 via path 430 to activity block 432 wherein the inspired and expired sums are divided by the number of elements forming the respective sums, thus generating an average. Control then passes via path 434 to activity block 436. If there is no data in the inspired and expired sums control passes from decision block 428 via path 438 to activity block 440 wherein the inspired value is set by default to the previous inspired value. Control then passes via path 434 to activity block 436 wherein trend data are stored in the trend buffer, and the updated concentration values are placed on the paint queue for display as CPU time becomes available. The update routine then terminates, returning to the main program decision block 440 via path 439.

Figure 9:
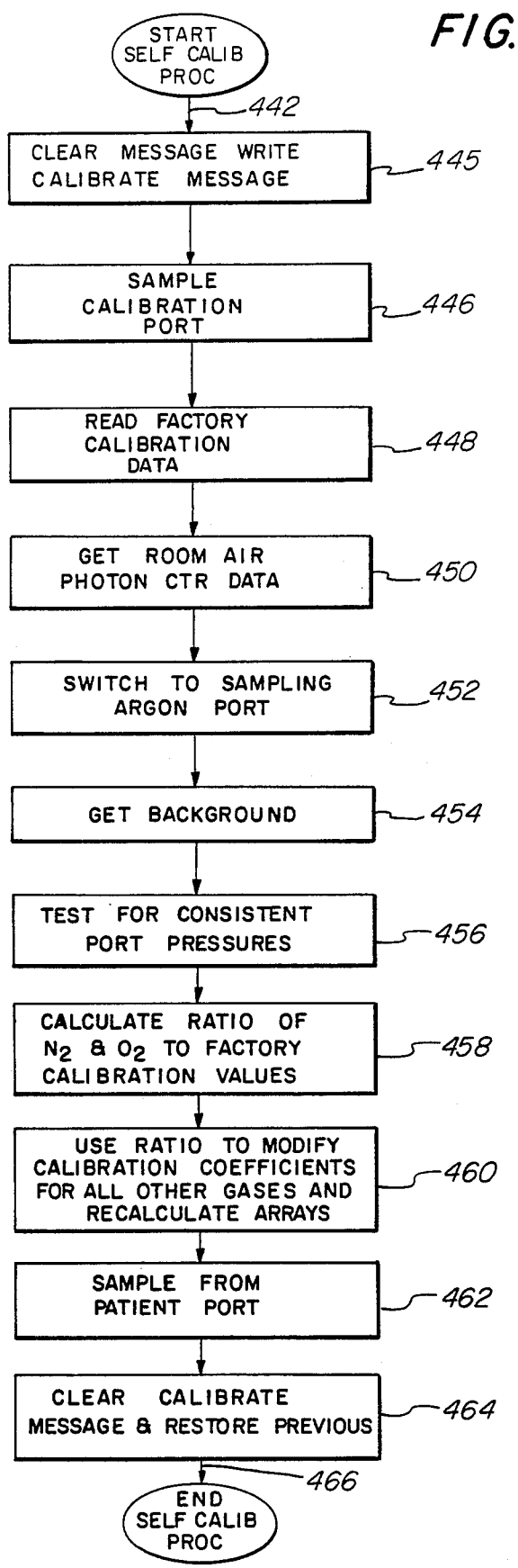
FIG. 9 is a flowchart for the self calibration procedure.

If it is time for a self-calibration, which occurs every five minutes, the main program proceeds via path 442 to activity block 444 which performs a self-calibration procedure. The detailed flow chart of the self-calibration procedure is presented in FIG. 9. Entering the self-calibration routine via path 442 into activity block 445 wherein the current message is cleared and a calibration message is written. Control then passes to activity block 446 which connects a sample calibration port to the instrument. Proceeding to activity block 448, factory calibration data is read in from memory. In activity block 450, data is taken from a room air sample. After obtaining the room air sample, the instrument is switched to an argon sampling port in activity block 452 wherein an on-board argon tank supplies argon gas to the sampling port of the instrument. The argon gas is used in activity block 454 to obtain a background. In activity block 456, the sampling port pressures are tested for consistent values. The concentration of oxygen and nitrogen in the room air sample is fixed, so any change in the signals for oxygen and nitrogen as compared to their factory calibration values in activity block 458, causes an analogous change in the signals in the other channels. Then, in activity block 460 the oxygen and nitrogen signals are ratioed to their factory calibration values and this ratio is used to modify the calibration coefficients for all of the other gases. The sampling port is then switched to the patient port in activity block 462. In activity block 464, the system restores its status by clearing the calibrate message and returning to the main routine along control path 466.

Returning again to FIG. 6 at decision block 440, if it is not time to do a self-calibration, control is passed via line 466 to the decision block 308. If the system is ready to paint digital data on the display screen, control passes vial line 468 to activity block 470, which updates the digital information on the screen. A detailed flow chart of the paint screen software when displaying trend data is shown in FIG. 10.

Figure 10:
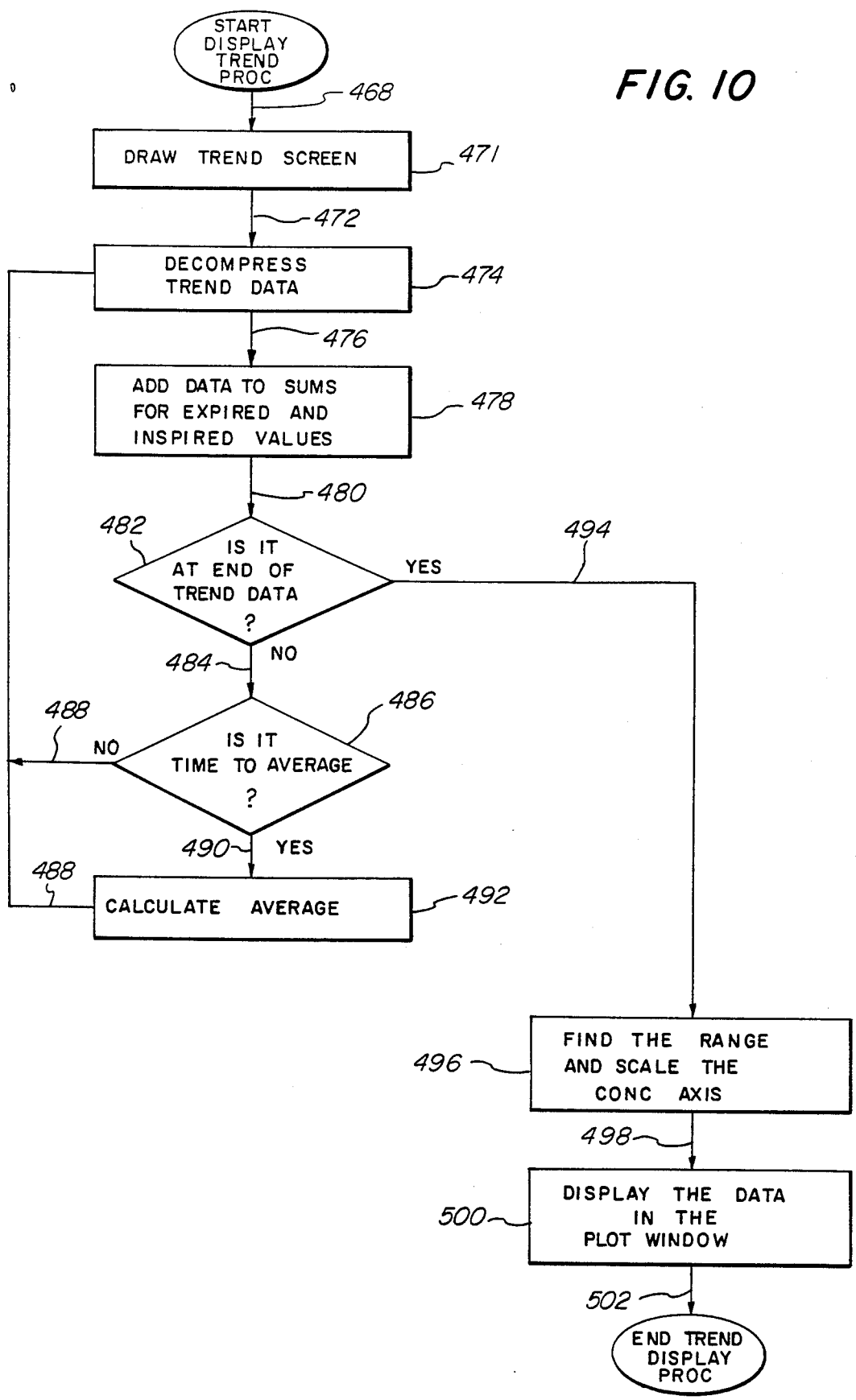
FIG. 10 is a flowchart for the display routine of the trend data.

Entering the first activity block 471 via path 468 in FIG. 10, the software draws the correct display and then proceeds via path 472 to activity block 474, wherein the trend data is extracted from the trend buffer. Control then passes via path 476 to activity block 478 wherein the data is added to the sums representing the expired and inspired values. Continuing via path 480 to decision block 482, if the end of the trend data has not been reached, control continues along path 484 to decision block 486. If it is not time to average the data, then control passes via line 488 back to activity block 474. The steps beginning with activity block 474 through decision block 486 continue until it is time to average the data, at which time control passes via path 490 to activity block 492 wherein the data are averaged. Control again passes via path 488 to activity block 474 and continues through decision block 482 until such time as the end of the trend buffer is reached. When this occurs, control transfers via path 494 to activity block 496 wherein the correct concentration scale is selected and displayed. Control then passes via path 498 to activity block 500 wherein the data for expired and inspired trend as a function of time are displayed in the plot window. Transfer then occurs via path 502 back to the main routine to decision block 312.

If the digital data is not ready to be painted on the screen at decision block 308 in FIG. 6, control is transferred directly via path 310 to activity block 312. In decision block 312, the keypad is read to see if any instructions have been received from the user to change the mode. If a key press has been received, control passes via path 504 to activity block 506 wherein the key press is parsed by comparing it to a list of mode change instructions for each key. These instructions primarily involve only the setting of global flags and redrawing the display. Control then returns via line 314 back to the starting decision block 304 of the main program infinite loop.

ALTERNATIVE MULTIPLE CELL CONFIGURATIONS

Referring again to FIG. 2, as an alternative to terminating the gas cell 50 with Brewster windows 102 and 106, if is possible to utilize Brewster window 98 on the plasma discharge tube 80 and mirror 108 at the end of the resonant cavity as the gas cell end windows. The gas sample is still constrained and, when properly designed, the cell volume can be minimized for adequate response time. A disadvantage is the risk of contamination to both Brewster window 98 and mirror 108. However, the potential for end window contamination is minimized in the preferred embodiment by incorporating a membrane-type filter (not shown) in a disposable interface tube preceding line 152 and filter housing 155 (shown in FIG. 4) connecting the patient to the detection system. As also shown in FIG. 4, a second membrane filter housing 155 and filter 156 upstream of the solenoid 149, gas cell 50 and pump 150 serves as additional protection against end window contamination. Finally, a second electronic barometer (not shown) may be conveniently located within the system to sense changes in atmospheric pressure necessary to accurately calculate the concentration of any gas in the sample in terms of millimeters of Hg.

It is also apparent from FIG. 2 that another intracavity gas cell (not shown) could be placed within the resonator cavity on the other side of plasma tube 80, between mirror 94 and Brewster window 96. FIG. 11 illustrates an expansion of this approach utilizing Brewster windows and resonator mirrors to define the ends of the gas cell and contain the gas sample within the resonator cavity. FIG. 11 broadly shows a laser 10, radiator 92, cathode 82, anode 84 and plasma tube 80 similar to those defined in FIG. 2. The intracavity laser beam is again indicated by numeral 78. Two intracavity cells, one on either side of plasma tube 80 are defined. The first cell is to the left of the plasma tube 80 being defined by mirror 94 and Brewster window 96. The second cell, to the right of plasma tube 80, being defined by Brewster window 98 and end mirror 108. It is apparent that sleeves 560 and 562 may contain side windows (not shown) in the same manner as gas cell 50 shown in FIG. 3. In the embodiment shown in FIG. 11, two additional windows 564 and 566 have been included within the left and right gas cells defined on either side of the plasma tube 80. The presence of these two end windows 564 and 566 effectively splits the resonating cavity of the laser into four intracavity gas cells which may be adapted for use in a manner similar to cell 50 shown in FIG. 2. Each of these four cells is illustrated in more detail in FIGS. 11a–11d.

FIG. 11a is a partial top section view of a portion 50a of FIG. 11 between mirror 94 and window 564. Sleeve 560 has been modified to contain side windows 146a through which the inelastic-scattered Raman light and Rayleigh scattered elastic laser light may be transmitted to optical filter-detector channels 60 in the same manner as previously described in conjuction with FIGS. 2, 3, and 5. The cell 50a is defined by mirror 94, end window 564 and housing 560 (modified sleeve) containing side windows 146. Adjacent mirror 94 and end window 564 are baffles 570 and 572 which serve to minimize scattered light from mirror 94 and end window 564 from entering the actual optical collection area.

FIG. 11b is a partial top section view of a portion 50b of FIG. 11 between window 564 and Brewster window 96 of plasma tube 80. Sleeve 560 has been modified to contain side windows 146b as described in conjuction with FIG. 11a. The cell 50b is defined by end window 564, Brewster window 96 and housing 560 (modified sleeve) containing side windows 146b. Adjacent end window 564 and Brewster window 96 are baffles 574 and 576 which serve to minimize scattered light from end window 564 and Brewster window 96 from entering the actual optical collection area.

FIG. 11c is a partial top section view of a portion of FIG. 11c between Brewster window 98 of plasma tube 80 and end window 566. Sleeve 562 has been modified to contain side windows 146c as described in conjuction with FIG. 119a. The cell 50c is defined by Brewster window 98, end window 566 and housing 562 (modified sleeve) containing side windows 146c. Adjacent Brewster window 98 and end window 566 are baffles 578 and 580 which serve to minimize scattered light from Brewster window 98 and end window 566 from entering the actual optical collection area.

FIG. 11d is a partial top section view of a portion of FIG. 11 between window 566 and end mirror 108.

Sleeve 562 has been modified to contain side windows 146d as described in conjuction with FIG. 11a. The cell 50d is defined by end window 566, end mirror 108 and housing 562 (modified sleeve) containing side windows 146d. Adjacent end window 566 and end mirror 108 are baffles 582 and 584 which serve to minimize scattered light from end window 566 and end mirror 108 from entering the actual optical collection area.

FIG. 11 also shows that a gas cell 50e, similar to that disclosed in FIG. 3, may be utilized in the extracavity mode outside the laser resonator. This cell 50e, as shown in the extracavity position in FIG. 11, consists of a housing 586, end windows 602 and 604 and side windows 164e which serve the same functions as described in FIGS. 1–3. In this case, extracavity beam 600 has to have sufficient optical power to generate detectable Raman scattered signals. End windows 602 and 604 confine the gas within the gas cell 50e and enable the extracavity beam to propagate through the cell 50e. Windows 602 and 604 are coated with a highly efficient narrowband anti-reflection coating, i.e., a "V" coating, for the particular wavelength of the laser. V-coating are multilayer dielectric anti-refelection coatings which reduce the reflectance of an optical component to rear-zero for one very narrow wavelength range, and are generally intended for use at normal or near-normal incidence. Hence, windows 602 and 604 are parallel to each other and substantially normal to the axis of the housing 586 and the laser beam 600. Such coatings will achieve maximum reflectances of not more than about 0.25% and are generally effective to allow only about 0.1% reflectance per surface at the specified wavelength. Thus, they do not appreciably interfere with the transmission of the laser beam through the resonating cavity of the laser. Alternatively, the end windows 602 and 604 may be uncoated fused silica oriented at Brewster's angle.

The system and process described herein were developed primarily for monitoring respiratory and anesthetic agent gases. However, it may also be useful for monitoring blood and tissue gases (in conjuction with a suitable sampling catheter), gases used for lung function and cardiac output determinations and hazardous gases in the workplace, and for detecting leaks in chemical process plants, monitoring levels of suspected chemical and environmental pollutants and in other applications where polyatomic gaseous molecules are to be detected and measured.

While the above description comprises one preferred embodiment of the invention as applied to the analysis of respiratory gases, there are others which will be obvious to those skilled in the art. Additionally, one skilled in the art will readily appreciate that the versatility and adaptability of the system makes it useful for numerous types of Raman spectroscopy analyses, such as pollution monitoring, chemical processing monitoring, and the like.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A apparatus for the simultaneous analysis and quantification of selected multiple polyatomic gases in a gas sample by Raman light scattering, comprising:
a source of laser light capable of producing a laser beam along a longitudinal axis of a selected wavelength comprising a laser resonant cavity, said laser resonant cavity comprising a plasma tube and wherein one end of said laser resonant cavity contains an output coupler mirror and the other end contains a high reflectivity mirror which does not transmit light;
gas sampling cell means for containing said gas sample at multiple locations along said longitudinal axis so that said laser beam is incident upon said gas sample at said multiple locations, said cell means defining a longitudinal gas constraining chamber having end optical means interconnected by a sidewall, said cell means being oriented relative to said laser cavity such that when said laser beam is activated, the laser beam is coincident with and traverses the axis of said longitudinal gas chamber, said optical end means being positioned to reflect or transmit a laser beam along the axis of the longitudinal gas chamber, said cell means also having opposing, aligned side windows in said sidewall parallel to and on either side of the axis of said longitudinal gas chamber; and
a series of optical filter-detection channels for simultaneously acquiring a plurality of samples of the optical energy scattered out of said beam incident upon samples from said multiple locations along said longitudinal axis, the optical portions of said channels being longitudinally aligned on either side of said cell means positioned parallel to and in alignment with said side windows, each of said optical filter-detection channels comprising:
an optical portion comprising a collection lens means positioned parallel to and in alignment with said laser beam and side windows outside same cell means to collect elastic laser scattered light and inelastic Stokes or antiStokes Raman scattered light passing through said side windows;
a filter portion comprising an interference filter means adapted to receive signals of both inelastic Stokes or anti-Stokes Raman scattered light and elastic laser scattered light passing through each such optical portion and transmit a single Stokes or anti-Stokes Raman line of a predetermined wavelength while rejecting scattered elastic laser light signals and all other signals of Stokes and anti-Stokes inelastic Raman scattered light; and
a detection portion comprising detection and amplification means for receiving Stokes or anti-Stokes Raman signals passing through said filter portion and converting said signals to digital electrical pulses, currents or voltages.

2. A device for the analysis of gases in a gas sample utilizing Raman light scattering, comprising:
a light source for producing a beam of optical radiation along a longitudinal axis;
a means for containing said gas sample at multiple locations along said longitudinal axis so that said beam of optical radiation is incident upon said gas sample at said multiple locations; and
a plurality of optical detector channels for simultaneously acquiring a plurality of samples of the optical energy scattered out of said beam incident upon samples from said multiple locations along said longitudinal axis.

3. A device as defined in claim 2, wherein said beam of optical radiation is substantially collimated while incident upon said gas sample at said multiple locations.

4. An apparatus as defined in claim 2, wherein a focusing means causes said optical radiation to form a substantially focused beam having multiple foci which are coincident with said multiple longitudinal locations.

5. A device as defined in claim 2, wherein said light source comprises a laser having a resonant cavity.

6. A device as defined in claim 5, wherein said multiple locations for containing said gas sample comprise a portion of said resonant cavity.

7. A device as defined in claim 5, wherein said multiple locations for containing said gas sample are located external to said resonant cavity.

8. A device as defined in claim 5, wherein at least one of said multiple locations for containing said gas sample comprises a portion of said resonant cavity and the remainder of said locations are external to said cavity.

9. A device as defined in claim 2, wherein said means for containing said gas sample comprises a gas cell having a chamber, said chamber having a longitudinal axis which is substantially coincident with said beam of optical radiation longitudinal axis.

10. A device as defined in claim 2, wherein said means for containing said gas sample comprises a gas cell having said multiple chambers, said multiple chambers located at said multiple locations along said beam of optical radiation longitudinal axis.

11. A device as defined in claim 2, further comprising a data analysis system which receives and analyzes signals from said detector channels representative of said scattered optical energy from said gas sample.

12. A device as defined in claim 11, wherein said data analysis system further comprises an output display for outputting the identity and concentration of specific gases comprising said gas sample.

13. A device as defined in claim 2, wherein said optical detector channels comprise:
a line rejection filter for attenuating elastically scattered or Rayleigh light;
a narrowband filter which transmits only optical signals within a narrow wavelength band corresponding to a particular Raman line of interest; and
a photon detector for receiving optical signals which are transmitted through said line rejection filter and said narrowband filter.

14. A device as defined in claim 13, wherein said line rejection filter and said narrowband filter are interference filters.

15. A device as defined in claim 13, wherein said photon detector comprises a photomultiplier tube (PMT).

16. A device as defined in claim 13, wherein said photon detector comprises a light sensitive solid state diode.

17. A device as defined in claim 2, wherein said optical detector channels comprise:
a narrowband filter which selects optical signals within a narrow wavelength band corresponding to one or more particular Raman lines of interest; and
a photon detector for receiving optical signals which are selected by said narrowband filter.

18. A device for analyzing a sample utilizing Raman spectroscopy comprising:
   a light source for producing optical energy;
   a collimator means for collimating said optical energy from said light source into a collimated beam of optical radiation propagating along an optical axis, said collimated beam of radiation comprising substantially parallel light rays along a region of said optical axis wherein said collimated beam interacts with said sample;
   a sample container for holding said sample to be analyzed in said interaction region; and
   multiple detector channels positioned at a plurality of locations within said interaction region of said optical axis for detecting light scattered out of said collimated beam by said sample at said plural locations.

19. A device as defined in claim 18, wherein said collimated beam of optical radiation is linearly polarized thus defining a polarization vector, said polarization vector and said optical axis of propagation additionally defining a plane of polarization.

20. A device as defined in claim 19, wherein said detector channels preferentially receive light which is propagating along an axis of detection and said axis of detection is oriented substantially perpendicular to said plane of polarization.

21. A device for analyzing a sample utilizing Raman scattered light comprising:
   a light source;
   multiple optical elements for focusing a beam of light from said light source thus creating multiple regions of increased intensity along said beam wherein light rays entering said regions substantially converge at said regions and light rays exiting said regions substantially diverge, said multiple regions lying along an optical axis in the general direction of propagation of said beam;
   a sample container for hold said sample within said high intensity regions so that said light beam interacts with said sample; and
   multiple detectors for detecting light scattered out of said beam by said sample at said multiple high intensity regions.

22. A device as defined in claim 21, wherein said light source generates unpolarized light.

23. A device as defined in claim 21, wherein said light source comprises a laser having a resonant cavity and wherein said sample container is located within said resonant cavity.

24. A system for the simultaneous analysis and quantification of selected multiple polyatomic gases in a gas sample by Raman light scattering, comprising:
   a source of laser light capable of producing a polarized laser beam of a selected wavelength comprising a laser resonant cavity, said laser resonant cavity comprising a plasma tube and wherein one end of said laser resonant cavity contains an output coupler mirror and the other end contains a high reflectivity mirror which does not transmit light;
   gas sampling cell means defining a longitudinal gas constraining chamber having end optical means interconnected by a sidewall, said cell means being oriented relative to said laser cavity such that when said laser beam is activated, the laser beam is coincident with and traverses the axis of said longitudinal gas chamber, said optical end means being positioned to reflect or transmit a laser beam along the axis of the longitudinal gas chamber, said cell means also having opposing, aligned side windows in said sidewall parallel to and on either side of the axis of said longitudinal gas chamber;
   a series of optical filter-detection channels, the optical portions of said channels being longitudinally aligned on either side of said cell means positioned parallel to and in alignment with said side windows, each of said optical filter-detection channels comprising:
      an optical portion comprising a collection lens means positioned parallel to and in alignment with said laser beam and side windows outside said cell means to collect elastic laser scattered light and inelastic Stokes or anti-Stokes Raman scattered light passing through said side windows:
      a filter portion comprising an interference filter means adapted to receive signals of both inelastic Stokes or anti-Stokes Raman scattered light and elastic laser scattered light passing through each such optical portion and transmit a Single Stokes or anti-Stokes Raman line of a predetermined wavelength while rejecting scattered elastic laser light signals and all other signals of Stokes and anti-Stokes inelastic Raman scattered light; and
      a detection portion comprising detection and amplification means for receiving Stokes or anti-Stokes Raman signals passing through said filter portion and converting said signals to digital electrical pulses, currents or voltages;
   processing mean for interpreting said digital electrical pulses, currents or voltages from each channel and converting them to visual readouts indicative of the concentration of each of said selected polyatomic molecular gases in said sample; and
   power means to operate said laser means, each optics filter-detection channel, amplification means and processing means.

25. A system according to claim 24, wherein said interference filter means comprises:
   laser line rejection filter means selected to reject elastic laser scattered light passing through said collection lens means while allowing the transmission of inelastic Stokes or anti-Stokes Raman scattered light; and
   line pass filter means selected to transmit only a single Stokes or anti-Stokes Raman spectral line of a predetermined wavelength.

26. A system according to claim 25, wherein laser line rejection filter means is positioned in said channel to precede said line pass filter means.

27. A system according to claim 25, wherein said line pass filter means is positioned in said channel to precede said laser line rejection filter.

28. A system according to claim 25, wherein each line pass filter is specific to the transmission of a different Stokes or anti-Stokes Raman wavelength indicative of a difference polyatomic gas.

29. A system according to claim 24, wherein said cell means further contains inlet and outlet means communicating with said chamber to pass a sample gas through said cell.

30. A system according to claim 29, wherein said cell means is a separate cell having opposing parallel end windows interconnected by a continuous sidewall, said end windows and sidewalls defining the longitudinal gas chamber, said end windows being positioned to be substantially normal to the axis of the longitudinal gas cell chamber.

31. A system according to claim 29, wherein said cell means is a separate cell having end windows interconnected by a continuous sidewall, said end windows and sidewalls define the longitudinal gas chamber, said end windows being positioned to be substantially at Brewster's angle with respect to the axis of the longitudinal gas cell chamber.

32. A system according to claim 30, wherein said end windows are coated with an anti-reflection coating specific to the selected wavelength of the laser beam.

33. A system according to claim 31, wherein said gas cell is positineed outside the laser resonant cavity.

34. A system according to claim 31, wherein said gas cell is positioned inside the laser resonant cavity.

35. A system according to claim 34, wherein said gas cell is positioned between the output coupler mirror and the adjacent end of the plasma tube.

36. A system according to claim 34, wherein said gas cell is positioned between the high reflectivity mirror and the adjacent end of the plasma tube.

37. A system according to claim 24, wherein said side windows in said gas cell are coated with a broadband antireflection coating adapted to pass desired wavelengths of inelastic Raman scattered light.

38. A method for the simultaneous and near instantaneous determination of the concentration of multiple polyatomic gas molecules in the gas sample, comprising:
   providing a laser means capable of producing a polarized laser beam of a selected wavelength comprising a laser resonant cavity, said laser resonant cavity comprising a plasma tube, and wherein one end of said laser resonant cavity comprises an output coupler mirror and the opposite end comprises a high reflectivity mirror;
   introducing said gas sample into a gas sampling cell means defining a longitudinal gas-constraining chamber having end optical means interconnected by a sidewall, said cell means being oriented relative to said laser cavity such that, when said laser beam is activated, the laser beam is coincident with and traverses the axis of said longitudinal gas chamber, said optical end means being positioned to reflect or transmit a laser beam along the axis of the longitudinal gas chamber, said cell means also having opposing, aligned side windows in said sidewall parallel to and on either side of the axis of said longitudinal gas chamber;
   subjecting said gas sample in said cell means to a laser beam of selected wavelength and polarization having sufficient intensity to produce detectable signals of inelastic Stokes or anti-Stokes raman scattered light;
   subjecting signals of either inelastic Stokes or anti-Stokes Raman scattered light and elastic laser scattered light to the optical portion of a series of optical filter-detection channels said optical portion of said channels being longitudinally aligned on either side of said cell means positioned parallel to and in alignment with said side windows and also having an optical axis which is substantially perpendicular to the axis to said laser beam;
   collecting signals of elastic laser scattered light and inelastic Stokes and anti-Stokes Raman scattered light by said optical portion of said channels;
   directing said signals of either inelastic Stokes or anti-Stokes Raman scattered light and elastic laser scattered light passing through such optical portion onto said filter portion of said channels, wherein a single Stokes or anti-Stokes Raman line of a predetermined wavelength is transmitted through said filter portion, and wherein scattered elastic laser light signals and all other signals of Stokes and anti-Stokes inelastic Raman scattered light are rejected;
   sensing each single Stokes or anti-Stokes Raman line signal passing through each filter system by said detection portion of said channels, wherein said signals are detected, amplified and converted into digital electrical pulses, current or voltage; and
   processing said digital electrical pulses from each optical filter-detection channel in processing means and converting them to visual readouts indicative of the concentration of each of said polyatomic molecules in said gas sample being determined.

39. A method according to claim 38, werein said polyatomic gases are members selected from the group consisting of respiratory and anesthetic gases.

40. A method according to claim 39, wherein said polyatomic gases are members selected from the group consisting of nitrogen, oxygen, carbon dioxide, nitrous oxide and the halogenated anesthesia gases.

41. A method according to claim 40, wherein said gases are sampled by means connected to the airway of a patient.

42. A method according to claim 39, wherein the gas sample is contained in cell means having inlet and outlet means communicating with said chamber to pass a sample gas through said cell means.

43. A method according to claim 42, wherein sample gas is continuously passed through said inlet and outlet means in said gas cell means by pump means located in a gas supply line on said outlet side of said gas cell means.

44. A method according to claim 39, wherein each optical filter-detection channels comprises:
   an optical portion made up of collection lens means;
   a filter portion, comprising:
      laser line rejection filter means selected to reject elastic laser scattered light passing through said collection lens means while allowing the transmission of inelastic Stokes or antiStokes Raman scattered light; and
      line pass filter means selected to transmit only a single Stokes or anti-Stokes Raman spectral line of a predetermined wavelength; and
   a detection portion consisting of detection and amplification means.

45. A method according to claim 44, wherein said cell means is a separate cell having opposing parallel end windows interconnected by a continuous sidewall, said end windows and sidewall defining the longitudinal gas chamber, said end windows being positioned to be substantially normal to the axis of the longitudinal gas cell chamber.

46. A method according to claim 45, wherein said end windows in said gas sampling cell are coated with an anti-reflection coating specific to the wavelength of the laser beam.

47. A method according to claim 45, wherein said gas cell is positioned outside said laser resonant cavity.

48. A method according to claim 45, wherein said gas cell is positioned inside said laser resonant cavity.

49. A method according to claim 48, wherein said gas cell is positioned between said output coupler mirror and the adjacent end of said plasma tube.

50. A method according to claim 48, wherein said gas cell is positioned between said high reflectivity mirror and the adjacent end of said plasma tube.

51. A method according to claim 44, wherein each line pass filter is specific to the transmission of different Stokes or anti-Stokes Raman wavelengths indicative of different polyatomic gases.

52. A method according to claim 44, wherein a focusing lens is positioned between the filter portion and the detector portion of each channel.

53. A method of analyzing a gas sample comprising:
producing a beam of optical radiation which propagates along a longitudinal axis;
confining said gas sample in a region along said longitudinal axis so that said beam of radiation propagates through said sample; and
collecting Raman scattered light which results from the interaction of said beam of radiation with said gas sample from multiple regions located along said longitudinal axis.

54. A method as defined in claim 53, further comprising the step of substantially collimating said beam of radiation within said multiple regions.

55. A method as defined in claim 53, further comprising the step of focusing said beam of radiation to form regions of high intensity at said multiple regions.

56. A method as defined in claim 53, wherein said beam of radiation comprises a laser beam and is generated by a laser having a resonant cavity, said method further comprising the step of placing said multiple regions within said resonant cavity.

57. A method as defined in claim 53, further comprising the step of analyzing said Raman scattered light to identify and quantify the molecular species of gases comprising said gas sample.

* * * * *

UNITED STATES PATENT AND TRADEMARK OFFICE
CERTIFICATE OF CORRECTION

PATENT NO. : 4,784,486

DATED : November 15, 1988

INVENTOR(S) : Van Wagenen, et al.

Page 1 of 2

It is certified that error appears in the above-identified patent and that said Letters Patent is hereby corrected as shown below:

Column 3, line 34, change "again precise" to -- again in reverse order. This elaborate scheme requires the precise--.

Column 6, line 61, change "collicated" to --collimated--.

Column 7, line 51, change "collicators' to --collimators--.

Column 8, line 14, change "YZ-pane" to --YZ-plane--.

Column 8, line 26, change "vector ol" to --vector o$\ell$--.

Column 8, lines 34 and 35, change "directions Om and ol" to --directions Om and o$\ell$--.

Column 8, line 47, change "number and $f(a^2$, of" to --number of--.

Column 8, line 48, change "state $v_i \gamma^2$," to --state $v_i$ and $f(a^2, \gamma^2,$--.

Column 11, line 3, change "199" to --119--.

Column 11, line 9, change "high relectivity" to --high reflectivity--.

Column 12, line 21, change "has" to --gas--.

Column 13, line 58, change "vial" to --via--.

Column 14, line 14, change "slide" to --slid--.

Column 14, line 56, change "the" to --The--.

Column 15, line 18, change "ot" to --to--.

UNITED STATES PATENT AND TRADEMARK OFFICE
CERTIFICATE OF CORRECTION

PATENT NO. : 4,784,486

DATED : November 15, 1988

INVENTOR(S) : Van Wagenen et al.

It is certified that error appears in the above-identified patent and that said Letters Patent is hereby corrected as shown below:

Column 17, line 14, change "60. each" to --60. Each--.

Column 17, line 52, add to Table I --C-H stretch    2950-3050    -   --.

Column 18, line 46, change "date" to --data--.

Column 22, line 5, change "vial" to --via--.

Column 24, line 14, change "164e" to --146e--.

Column 24, lines 24 and 25, change "rear-zero" to --near-zero--.

Column 27, line 39, change "hold" to --holding--.

Column 29, line 15, change "positioneed" to --positioned--.

Signed and Sealed this

Fifteenth Day of August, 1989

*Attest:*

DONALD J. QUIGG

*Attesting Officer*   Commissioner of Patents and Trademarks